(12) United States Patent
Xie et al.

(10) Patent No.: US 8,372,854 B2
(45) Date of Patent: Feb. 12, 2013

(54) PYRROLO[2,3-D]PYRIMIDINE COMPOUNDS

(75) Inventors: Jin Xie, Ballwin, MO (US); Michele Ann Promo, Albany, GA (US); Eric Jon Jacobsen, Chesterfield, MO (US); Horng-Chih Huang, Chesterfield, MO (US); Todd M. Maddux, Kalamazoo, MI (US)

(73) Assignee: Pfizer Inc., Madison, NJ (US)

( * ) Notice: Subject to any disclaimer, the term of this patent is extended or adjusted under 35 U.S.C. 154(b) by 62 days.

(21) Appl. No.: 12/964,841

(22) Filed: Dec. 10, 2010

(65) Prior Publication Data
US 2011/0294826 A1 Dec. 1, 2011

Related U.S. Application Data

(60) Provisional application No. 61/287,924, filed on Dec. 18, 2009.

(51) Int. Cl.
A01N 43/90 (2006.01)
A61K 31/519 (2006.01)
C07D 487/00 (2006.01)

(52) U.S. Cl. .................................. 514/265.1; 544/280
(58) Field of Classification Search .................. None
See application file for complete search history.

(56) References Cited

U.S. PATENT DOCUMENTS

| 2006/0293311 A1 | 12/2006 | Li et al. |
| 2007/0203162 A1 | 8/2007 | Li et al. |
| 2007/0207995 A1 | 9/2007 | Salituro et al. |
| 2007/0259904 A1 | 11/2007 | Noronha et al. |

FOREIGN PATENT DOCUMENTS

| WO | WO 99/65908 A1 | 12/1999 |
| WO | WO 99/65909 A1 | 12/1999 |
| WO | WO 01/42246 A2 | 6/2001 |
| WO | WO 02/096909 A1 | 12/2002 |
| WO | WO 2004/046112 A2 | 6/2004 |
| WO | WO 02/00661 A1 | 2/2007 |
| WO | WO 2007/012953 A2 | 2/2007 |
| WO | WO 2007/041130 A2 | 4/2007 |
| WO | WO 2007/077949 A1 | 7/2007 |
| WO | WO 2008/090181 A1 | 7/2008 |
| WO | WO2010/020905 * | 2/2010 |
| WO | WO 2010/020905 A1 | 2/2010 |

OTHER PUBLICATIONS

Kisseleva, T., et al.; Gene 285, pp. 1-24, 2002.
Yamaoka, Kunihiro, et al; Genome Biology, 5:253, 2004.
Handbook of Pharmaceutical Salts: Properties, Selection, and Use by Stahl and Werrnuth (Wiley-VCH, 2002).
Polymorphism in Pharmaceutical Solids by K.R. Morris (Ed. H.G. Brittain, Marcel Dekker, 1995).
O. Almarsson and M.J. Zaworotko; Chem. Commun., 17, pp. 1889-1896, 2004.
J.K. Haleblian; Journal of Pharmaceutical Sciences, 64: 8, pp. 1269-1288, Aug. 1975.
Crystals and the Polarizing Microscope by N.H. Hartshorne and A. Stuart, 4th Edition (Edward Arnold, 1970).
Bioreversible Carriers in Drug Design, Pergamon Press, 1987 (Ed. E.B. Roche, American Pharmaceutical Association).
Design of Pro-drugs by H. Bundgaard (Elsevier, 1985).
Stereochemistry of Organic Compounds by E.L. Eliel and S.H. Wilen (Wiley, 1994).
Barrie C. Finnin and Timothy M. Morgan; Journal of Pharmaceutical Science, 88 (10), pp. 955-958, (Oct. 1999).
"Remingtons Pharmaceutical Sciences", Mack Pub. Co., New Jersey (1991).
Frank, David A.; Molecular Medicine 5: pp. 432-456, 1999.
Suzuki, Kotaro, et al.; Blood. 96: pp. 2172-2180, (2000).
Seidel, H. Martin, et al.; Oncogene 19: pp. 2645-2656, 2000.
Malaviya, Ravi, et al.; Biochemical and Biophysical Research Communications 257, pp. 807-813 (1999).
Malaviya, Ravi, et al.; The Journal of Biological Chemistry, vol. 274, No. 38, Issue of Sep. 17, pp. 27028-27038, 1999.
Kirken, R.A.; Transplantation Proceedings, 33, 3268-3270 (2001).
Muller-Ladner, Ulf, et al.; The Journal of Immunology 2000, 164, pp. 3894-3901.
Trieu, Vuong N., et al,: Biochemical and Biophysical Research Communications 267, pp. 22-25 (2000).
Sudbeck, Elise A., et al.; Clinical Cancer Research, 5: pp. 1569-1582 (1999).
Nielsen, Mette, et al.; Proc. Natl. Acad. Sci. USA, vol. 94, pp. 6764-6769, Jun. 1997.
Yu, Chao-Lan, et al.; Journal of Immunology, 159: pp. 5206-5210, (1997).
Catlett-Falcone, Robyn, et al., Immunity, vol. 10, pp. 105-115, Jan. 1999.
Demoulin, Jean-Baptiste, et al.; Molecular and Cellular Biology, vol. 16, No. 9, pp. 4710-4716, (1996).
Jurlander, Jesper, et al.: Blood, 89, pp. 4146-4152 (1997).
Kaneko, S., et al.; Clin. Exp. Immun., 109: pp. 185-183(1997).
Nakamura, Norihiko, et al.; The Journal of Biological Chemistry, vol. 271, No. 32, Issue of Aug. 9, pp.19483-19488, 1996. Kudiacz, Elizabeth, et al.; American Journal of Transplantation 2004: 4: pp. 51-57.
Changelian, Paul S., et al.; Science 302, 875 (2003).
"Protective Groups in Organic Synthesis" by TW Greene and PGM Wuts, John Wiley & Sons, Inc., (1999).
"Handbook of Reagents for Organic Synthesis—Oxidising and Reducing Agents" edited by S.D. Burke and R.L. Danheiser, John Wiley & Sons, Inc., (1999).

* cited by examiner

Primary Examiner — Jeffrey Murray
(74) Attorney, Agent, or Firm — A. David Joran

(57) ABSTRACT

Described herein are pyrrolo[2,3-d]pyrimidine compounds, their use as Janus Kinase (JAK) inhibitors, pharmaceutical compositions containing these compounds, and methods for their preparation.

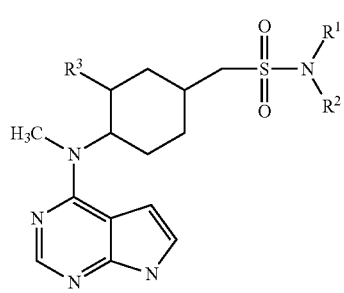

Formula I

26 Claims, No Drawings

PYRROLO[2,3-D]PYRIMIDINE COMPOUNDS

FIELD OF THE INVENTION

The present invention provides pharmaceutically active pyrrolo[2,3-d]pyrimidine compounds and analogues. Such compounds are useful for inhibiting Janus Kinase (JAK). This invention also is directed to compositions comprising methods for making such compounds, and methods for treating and preventing conditions mediated by JAK.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, overexpression, or inappropriate regulation, dysregulation or deregulation, as well as over or under production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

Thus, protein kinases have emerged as an important class of enzymes as targets for therapeutic intervention. In particular, the JAK family of cellular protein tyrosine kinases (Jak1, Jak2, Jak3, and Tyk2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the IFN family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23), gammaC family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

There remains a need for alternative compounds that effectively inhibit JAK enzymes, including JAK1, JAK2, JAK3, and/or Tyk2.

SUMMARY OF THE INVENTION

This invention is directed, in part, to compounds that generally fall within the structure of Formula I:

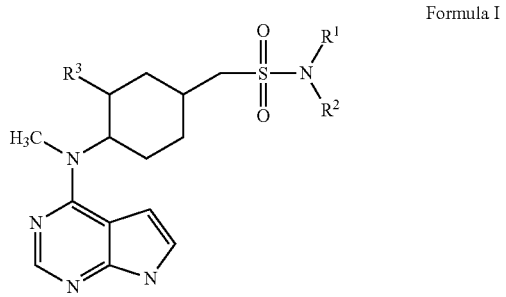

Formula I or a pharmaceutically acceptable salt thereof; wherein:

$R^1$ is selected from the group consisting of hydrogen and $(C_1-C_6)$alkyl; and when $R^1$ is hydrogen, then $R^2$ is selected from the group consisting of $(C_5-C_6)$alkyl, halo$(C_1-C_6)$alkyl, $(C_3-C_6)$cycloalkyl$(C_1-C_6)$alkyl, hydroxy$(C_5-C_6)$alkyl, $(C_1-C_6)$alkenyl, halo$(C_1-C_6)$alkenyl, phenyl, phenyl$(C_1-C_6)$alkyl, $(C_3-C_6)$cycloalkl, heterocyclyl, and heterocyclyl$(C_1-C_6)$alkyl;

when $R^1$ is $(C_1-C_6)$alkyl, then $R^2$ is selected from the group consisting of $(C_1-C_6)$alkyl, halo$(C_1-C_6)$alkyl, $(C_3-C_6)$cycloalkyl$(C_1-C_6)$alkyl, hydroxy$(C_1-C_6)$alkyl, $(C_1-C_6)$alkenyl, phenyl, phenyl$(C_1-C_6)$alkyl, $(C_3-C_6)$cycloalkyl, heterocyclyl, and heterocyclyl$(C_1-C_6)$alkyl;

wherein $(C_3-C_6)$cycloalkyl, wherever it occurs, is optionally substituted with one or more substituents selected from the group consisting of hydroxy$(C_1-C_6)$alkyl, phenyl, phenyl$(C_1-C_6)$alkyl, and $(C_1-C_6)$alkoxycarbonylamino; and wherein when $R^1$ is hydrogen and $R^2$ is cyclobutyl, then the cyclobutyl is substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino;

wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, aminosulfonyl, and $(C_1-C_6)$alkylaminosulfonyl;

wherein heterocyclyl, wherever it occurs, is optionally substituted with one or more substituents independently selected from the group consisting of halo, $(C_1-C_6)$alkyl, $(C_1-C_6)$alkoxy, amino, and $(C_1-C_6)$alkylamino; and wherein the $(C_1-C_6)$alkyl in phenyl$(C_1-C_6)$alkyl and heterocyclyl$(C_1-C_6)$alkyl is optionally substituted with one more substituents independently selected from the group consisting of halo and hydroxy; and $R^3$ selected from the group consisting of hydrogen and $(C_1-C_6)$alkyl.

DETAILED DESCRIPTION

The invention will be more carefully understood from the following description given by way of example only. The present invention is directed to a class of pyrrolo[2,3-d]pyrimidine compounds. In particular, the present invention is directed to pyrrolo[2,3-d]pyrimidine compounds useful as inhibitors of JAK. While the present invention is not so limited, an appreciation of various aspects of the invention will be gained through the following discussion and the examples provided below.

DEFINITIONS

The following is a list of definitions of various terms used herein:

The symbol ∿∿ represents the point of attachment.

The term "alkyl" refers to a hydrocarbon radical having a straight or branched chain or combinations thereof. Alkyl radicals can be a univalent, a bivalent or a cyclic radical. Examples of univalent alkyl radicals are methyl, ethyl, n-propyl, isopropyl, n-butyl, isobutyl, sec-butyl, t-butyl, pentyl, neopentyl, hexyl, isohexyl, and the like. Examples of bivalent alkyl radicals include

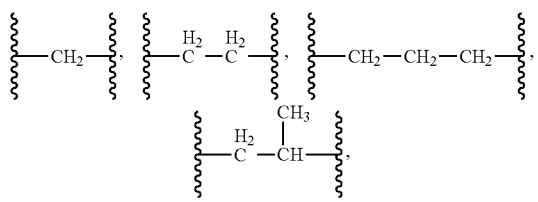

and the like. Examples of cyclic alkyl radicals include cyclopropyl, cyclobutyl, cyclopentyl, cyclohexyl, and the like.

The term "alkoxy" means alkyl-O—, wherein alkyl is as defined above. Examples of such a substituent include methoxy ($CH_3$—O—), ethoxy, n-propoxy, isopropoxy, n-butoxy, iso-butoxy, sec-butoxy, tert-butoxy and the like.

The term "cycloalkyl" means a saturated carbocyclyl substituent containing from 3 to about 20 carbon atoms, preferably containing from 3 to 8 carbon atoms. A cycloalkyl may be a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "aryl" means an aromatic carbocyclyl containing from 6 to 14 carbon ring atoms. The term aryl embraces both single and multiple rings. Examples of aryls include phenyl, naphthalenyl, and indenyl, and the like.

The term "arylalkyl" means alkyl substituted with aryl, wherein alkyl and aryl are as defined above.

The term alkylamino" means an alkyl substituted amino. The term embraces both monoalkyl and dialkyl substitution.

The term "carboxy" means OH—C(O)—, which also may be depicted as:

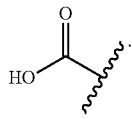

The symbol "C(O)" represents carbonyl which also may be depicted as:

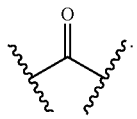

The term "oxo" means a double bonded oxygen, and may be depicted as =O.

The term "hydroxy" or "hydroxyl" means OH—.

The term "hydroxyalkyl" means alkyl substituted with one or more hydroxy, wherein hydroxy and alkyl are as defined above.

The term "halo" refers to bromo, chloro, fluoro or iodo.

The term "oxy" means an ether substituent, and may be depicted as —O—.

The term "sulfonyl" means $SO_2$—.

The term "thio" means HS—.

The term "alkylthio" is an alkyl substituted thio, which is also depicted as:

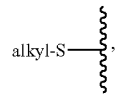

wherein thio and alkyl are as defined above.

The term "hydroxyalkyl" is a hydroxy substituted alkyl, examples include hydroxymethyl, hydroxyethyl and the like.

The term "haloalkyl" is an alkyl substituted with one or more halo, examples include fluoromethyl, bromomethyl, thrifluoromethyl, and the like.

The term "heterocyclyl" means an unsaturated, saturated or partially saturated ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. A heterocyclyl may also be 2 or 3 fused rings. Examples of heterocyclyls include azepanyl, diazepanyl, morpholinyl, piperidinyl, piperazinyl, pyrrolidinyl, tetrahydrofuranyl, tetrahydropyranyl, benzodioxolyl, benzofuranyl, furyl, indolyl, indazolyl, imidazolyl, isoxazolyl, oxadiazolyl, pyridazinyl, pyrimidinyl, pyrrolopyridinyl, pyrazolyl, pyrazinyl, pyridinyl, quinolinyl, tetrazolyl, thiazolidinyl, thiamorpholinyl, triazolyl, 3,4-dihydro-2H-benzo[b][1,4]dioxepinyl, 2,7diazaspiro[4.5]decanyl and the like.

If substituents are described as being "independently selected" from a group, each substituent is selected independent of the other. Each substituent therefore may be identical to or different from the other substituent(s).

The term "livestock" refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys.

The term "companion animal" refers to a pet or household animal. Examples of companion animals include but are not limited to dogs, cats, rodents including hamsters, guinea pigs, gerbils and the like, rabbits, ferrets and birds.

The phrase "therapeutically-effective" indicates the capability of an agent to prevent, or improve the severity of, the disorder, while avoiding adverse side effects typically associated with alternative therapies. The phrase "therapeutically-effective" is to be understood to be equivalent to the phrase "effective for the treatment, prevention, or amelioration", and both are intended to qualify the amount of each agent for use in the combination therapy which will achieve the goal of improvement in the severity of cancer, cardiovascular disease, or pain and inflammation and the frequency of incidence over treatment of each agent by itself, while avoiding adverse side effects typically associated with alternative therapies.

"Treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies. The compounds of the invention can also be administered in conjunction with other drugs and/or therapies.

Compounds of the Invention

Among its many embodiments, the present invention includes compounds or pharmaceutically acceptable salts thereof, having a structure according to formula I:

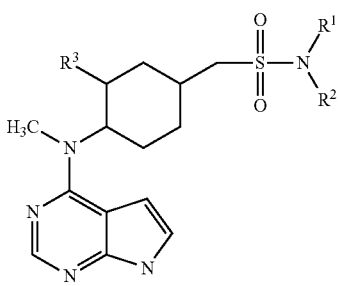

Formula I wherein:
- $R^1$ is selected from the group consisting of hydrogen and $(C_1-C_6)$alkyl; and
    - when $R^1$ is hydrogen, then $R^2$ is selected from the group consisting of $(C_6-C_6)$alkyl, halo$(C_1-C_6)$alkyl, $(C_3-C_6)$cycloalkyl$(C_1-C_6)$alkyl, hydroxy$(C_5-C_6)$alkyl, $(C_1-C_6)$alkenyl, halo$(C_1-C_6)$alkenyl, phenyl, phenyl$(C_1-C_6)$alkyl, $(C_3-C_6)$cycloalkyl, heterocyclyl, and heterocyclyl$(C_1-C_6)$alkyl;
    - when $R^1$ is $(C_1-C_6)$alkyl, then $R^2$ is, selected from the group consisting of $(C_1-C_6)$alkyl, halo$(C_1-C_6)$alkyl, $(C_3-C_6)$cycloalkyl$(C_1-C_6)$alkyl, hydroxy$(C_1-C_6)$alkyl, $(C_1-C_6)$alkenyl, phenyl, phenyl$(C_1-C_6)$alkyl, $(C_3-C_6)$cycloalkyl, heterocyclyl, and heterocyclyl$(C_1-C_6)$alkyl;
    - wherein $(C_3-C_6)$cycloalkyl, wherever it occurs, is optionally substituted with one or more substituents selected from the group consisting of hydroxy$(C_1-C_6)$alkyl, phenyl, phenyl$(C_1-C_6)$alkyl, and $(C_1-C_6)$alkoxycarbonylamino; and wherein when $R^1$ is hydrogen and $R^2$ is cyclobutyl, then the cyclobutyl is substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino;
    - wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, aminosulfonyl, and $(C_1-C_6)$alkylaminosulfonyl;
    - wherein heterocyclyl, wherever it occurs, is optionally substituted with one or more substituents independently selected from the group consisting of halo, $(C_1-C_6)$alkyl, $(C_1-C_6)$alkoxy, amino, and $(C_1-C_6)$alkylamino; and
    - wherein the $(C_1-C_6)$alkyl in phenyl$(C_1-C_6)$alkyl and heterocyclyl$(C_1-C_6)$alkyl is optionally substituted with one more substituents independently selected from the group consisting of halo and hydroxy; and
- $R^3$ selected from the group consisting of hydrogen and $(C_1-C_6)$alkyl.

In some embodiments, the present invention includes compounds or pharmaceutically acceptable salts thereof, having a structure according to formula I, wherein:
- $R^1$ is selected from the group consisting of hydrogen and $(C_1-C_6)$alkyl; and
    - when $R^1$ is hydrogen, then $R^2$ is selected from the group consisting of $(C_5-C_6)$alkyl, halo$(C_1-C_6)$alkyl, $(C_3-C_6)$cycloalkyl$(C_1-C_6)$alkyl, hydroxy$(C_6-C_6)$alkyl, halo$(C_1-C_6)$alkenyl, phenyl, phenyl$(C_1-C_6)$alkyl, cyclopropyl, cyclobutyl, cyclopentyl, cyclohexyl, indolyl, indazolyl, pyridinyl, pyrazolyl, 3,4-dihydro-2H-benzo[b][1,4]dioxepinyl, indolylmethyl, pyridinylmethyl, pyrimidinylmethyl, pyrazinylmethyl, pyrazolylmethyl, tetrahydrofuranylmethyl, and pyridinylethyl; and
    - when $R^1$ is $(C_1-C_6)$alkyl, then $R^2$ is selected from the group consisting of $(C_1-C_6)$alkyl, halo$(C_1-C_6)$alkyl, hydroxy$(C_1-C_6)$alkyl, phenyl, phenyl$(C_1-C_6)$alkyl, pyrazinylmethyl, and pyridinylmethyl;
    - wherein cyclopropyl, cyclobutyl, cyclopentyl, and cyclohexyl, wherever they occur, are optionally substituted with one or more substituents selected from the group consisting of hydroxy$(C_1-C_6)$alkyl, phenyl, phenyl$(C_1-C_6)$alkyl, and $(C_1-C_6)$alkoxycarbonylamino; and wherein when $R^1$ is hydrogen and $R^2$ is cyclobutyl, then the cyclobutyl is substituted with one or more substituents selected from the group consisting of hydroxy$(C_1-C_6)$alkyl, phenyl, phenyl$(C_1-C_6)$alkyl, and $(C_1-C_6)$alkoxycarbonylamino;
    - wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, and aminosulfonyl;
    - wherein indolyl, indazolyl, pyridinyl, pyrimidinyl, pyrazinyl, pyrazolyl, 3,4-dihydro-2H-benzo[b][1,4]dioxepinyl, and tetrahydrofuranyl, wherever they occur, are optionally substituted with one or more substituents independently selected from the group consisting of halo, $(C_1-C_6)$alkyl, $(C_1-C_6)$alkoxy, and amino; and
    - wherein the $(C_1-C_6)$alkyl in phenyl$(C_1-C_6)$alkyl is optionally substituted with one more substituents independently selected from the group consisting of halo and hydroxy; and
- $R^3$ selected from the group consisting of hydrogen and $(C_1-C_6)$alkyl.

In some embodiments, the present invention includes compounds or pharmaceutically acceptable salts thereof, having a structure according to formula I, wherein:
- $R^1$ is hydrogen;
- $R^2$ is selected from the group consisting of $(C_5-C_6)$alkyl, halo$(C_1-C_6)$alkyl, $(C_3-C_6)$cycloalkyl$(C_1-C_6)$alkyl, hydroxy$(C_5-C_6)$alkyl, $(C_1-C_6)$alkenyl, and halo$(C_1-C_6)$alkenyl;
    - wherein the $(C_3-C_6)$cycloalkyl in $(C_3-C_6)$cycloalkyl$(C_1-C_6)$alkyl is optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and
- $R^3$ selected from the group consisting of hydrogen and $(C_1-C_6)$alkyl.

In some embodiments, the present invention includes compounds or pharmaceutically acceptable salts thereof, having a structure according to formula I, wherein:
- $R^1$ is hydrogen;
- $R^2$ is selected from the group consisting of $(C_5-C_6)$alkyl, halo$(C_1-C_6)$alkyl, $(C_3-C_6)$cycloalkyl$(C_1-C_6)$alkyl, hydroxy$(C_5-C_6)$alkyl, $(C_1-C_6)$alkenyl, and halo$(C_1-C_6)$alkenyl;
    - wherein the $(C_3-C_6)$cycloalkyl in $(C_3-C_6)$cycloalkyl$(C_1-C_6)$alkyl is optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and
- $R^3$ selected from the group consisting of hydrogen and methyl.

In some embodiments, the present invention includes compounds or pharmaceutically acceptable salts thereof, having a structure according to formula I, wherein:

$R^1$ is hydrogen;

$R^2$ is selected from the group consisting of cyclopropylmethyl and trifluorobutenyl; and $R^3$ selected from the group consisting of hydrogen and methyl.

In one embodiment, the present invention includes compounds or pharmaceutically acceptable salts thereof, selected from the group consisting of N-(cyclopropylmethyl)-1-{cis-4-[methyl(7H-pyrrolo[2,3-d]pyrimidin-4-yl)amino]cyclohexyl}methanesulfonamide; and 1-{trans-4-[(methyl(7H-pyrrolo[2,3-d]pyrimidin-4-yl)amino]cyclohexyl}-N-(3,4,4-trifluorobut-3-en-1-yl)methanesulfonamide.

In one embodiment, the present invention includes compounds or pharmaceutically acceptable salts thereof, having a structure according to formula I, wherein $R^1$ is $(C_1-C_6)$alkyl;

$R^2$ is selected from the group consisting of $(C_1-C_6)$alkyl, halo$(C_1-C_6)$alkyl, $(C_3-C_6)$cycloalkyl$(C_1-C_6)$alkyl, hydroxy$(C_1-C_6)$alkyl, $(C_1-C_6)$alkenyl, and halo$(C_1-C_6)$alkenyl;

wherein the $(C_3-C_6)$cycloalkyl in $(C_3-C_6)$cycloalkyl$(C_1-C_6)$alkyl is optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and $R^3$ selected from the group consisting of hydrogen and $(C_1-C_6)$alkyl.

In some embodiments, the present, invention includes compounds or pharmaceutically acceptable salts thereof, having a structure according to formula I, wherein:

$R^1$ is $(C_1-C_6)$alkyl;

$R^2$ is selected from the group consisting of $(C_1-C_6)$alkyl, halo$(C_1-C_6)$alkyl, $(C_3-C_6)$cycloalkyl$(C_1-C_6)$alkyl, and hydroxy$(C_1-C_6)$alkyl;

wherein the $(C_3-C_6)$cycloalkyl in $(C_3-C_6)$cycloalkyl$(C_1-C_6)$alkyl is optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and $R^3$ selected from the group consisting of hydrogen and methyl.

In some embodiments, the present invention includes compounds or pharmaceutically acceptable salts thereof, having a structure according to formula I, wherein:

$R^1$ is $(C_1-C_6)$alkyl;

$R^2$ is selected from the group consisting of $(C_1-C_6)$alkyl and hydroxy$(C_1-C_6)$alkyl; and $R^3$ selected from the group consisting of hydrogen and $(C_1-C_6)$alkyl.

In some embodiments, the present invention includes compounds or pharmaceutically acceptable salts thereof, having a structure according to formula I, wherein:

$R^1$ is methyl;

$R^2$ is selected from the group consisting of methyl and hydroxyethyl; and $R^3$ selected from the group consisting of hydrogen and methyl.

In one embodiment, the present invention includes compounds or pharmaceutically acceptable salts thereof, selected from the group consisting of N-(2-hydroxyethyl)-N-methyl-1-{trans-4-[methyl(7H-pyrrolo[2,3-d]pyrimidin-4-yl)amino]cyclohexyl}methanesulfonamide;

N-[(6-aminopyridin-2-yl)methyl]-N-methyl-1-{trans-4-[methyl(7H-pyrrolo[2,3-d]pyrimidin-4-yl)amino]cyclohexyl}methanesulfonamide;

N-methyl-1-{trans-4-[methyl(7H-pyrrolo[2,3-d]pyrimidin-4-yl)amino]cyclohexyl}-N-(pyridin-3-ylmethyl)methanesulfonamide;

N-methyl-1-{trans-4-[methyl(7H-pyrrolo[2,3-d]pyrimidin-4-yl)amino]cyclohexyl}-N-(pyrazin-2-ylmethyl)methanesulfonamide; and N,N-dimethyl((1r,4r)-4-(methyl(7H-pyrrolo[2,3-d]pyrimidin-4-yl)amino)cyclohexyl)methanesulfonamide.

In one embodiment, the present invention includes compounds or pharmaceutically acceptable salts thereof, having a structure according to formula I, wherein:

$R^1$ is selected from the group consisting of hydrogen and $(C_1-C_6)$alkyl; and $R^2$ is selected from the group consisting of cyclopropyl, cyclobutyl, cyclopentyl, and cyclohexyl;

wherein cyclopropyl, cyclobutyl, cyclopentyl, and cyclohexyl are optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and wherein when $R^1$ is hydrogen and $R^2$ is cyclobutyl, then the cyclobutyl is substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and $R^3$ selected from the group consisting of hydrogen and $(C_1-C_6)$alkyl.

In some embodiments, the present invention includes compounds or pharmaceutically acceptable salts thereof, having a structure according to formula I, wherein:

$R^1$ is selected from the group consisting of hydrogen and $(C_1-C_6)$alkyl; and $R^2$ is selected from the group consisting of cyclopropyl, cyclobutyl, cyclopentyl, and cyclohexyl;

wherein cyclopropyl, cyclobutyl, cyclopentyl, and cyclohexyl are optionally substituted with one or more substituents selected from the group consisting of hydroxypropyl, phenyl, fluorophenyl, phenylmethyl and tert-butoxycarbonylamino; and wherein when $R^1$ is hydrogen and $R^2$ is cyclobutyl, then the cyclobutyl is substituted with one or more substituents selected from the group consisting of hydroxypropyl, phenyl, fluorophenyl, phenylmethyl and tert-butoxycarbonylamino; and $R^3$ selected from the group consisting of hydrogen and $(C_1-C_6)$alkyl.

In some embodiments, the present invention includes compounds or pharmaceutically acceptable salts thereof, having a structure according to formula I, wherein $R^1$ is hydrogen.

In some embodiments, the present invention includes compounds or pharmaceutically acceptable salts thereof, having a structure according to formula I, wherein $R^1$ is $(C_1-C_6)$alkyl.

In some embodiments, the present invention includes compounds or pharmaceutically acceptable salts thereof, having a structure according to formula I, wherein:

$R^1$ is selected from the group consisting of hydrogen and methyl; and $R^2$ is selected from the group consisting of cyclopropyl, cyclobutyl, cyclopentyl, and cyclohexyl;

wherein cyclopropyl, cyclobutyl, cyclopentyl, and cyclohexyl are optionally substituted with one or more substituents selected from the group consisting of hydroxypropyl, phenyl, fluorophenyl, phenylmethyl and tert-butoxycarbonylamino; and wherein when $R^1$ is hydrogen and $R^2$ is cyclobutyl, then the cyclobutyl is substituted with one or more substituents selected from the group consisting of hydroxypropyl, phenyl, fluorophenyl, phenylmethyl and tert-butoxycarbonylamino; and $R^3$ selected from the group consisting of hydrogen and methyl.

In some embodiments, the present invention includes compounds or pharmaceutically acceptable salts thereof, having a structure according to formula I, wherein:

$R^1$ is hydrogen;

$R^2$ is selected from the group consisting of cyclopropyl, fluorophenylcyclopentyl, hydroxypropylcyclohexyl, and tert-butoxycarbonylaminocyclobutyl; and $R^3$ selected from the group consisting of hydrogen and methyl.

In one embodiment, the present invention includes compounds or pharmaceutically acceptable salts thereof, selected from the group consisting of N-cyclopropyl-1-{trans-4-[methyl(7H-pyrrolo[2,3-d]pyrimidin-4-yl)amino]cyclohexyl}methanesulfonamide;

N-[trans-4-(1-hydroxy-1-methylethyl)cyclohexyl]-1-{trans-4-[methyl(7H-pyrrolo[2,3-d]pyrimidin-4-yl)amino]cyclohexyl}methanesulfonamide;

tert-butyl (3-{[({trans-4-[methyl(7H-pyrrolo[2,3-d]pyrimidin-4-yl)amino]cyclohexyl}methyl)sulfonyl]amino}cyclobutyl)carbamate;

N-[(1R,2R)-2-(4-fluorophenyl)cyclopentyl]-1-{trans-4-[methyl(7H-pyrrolo[2,3-d]pyrimidin-4-yl)amino]cyclohexyl}methanesulfonamide;

N-(1-benzylcyclobutyl)-1-{trans-4-[methyl(7H-pyrrolo[2,3-d]pyrimidin-4-yl)amino]cyclohexyl}methanesulfonamide; and 1-{trans-4-[methyl(7H-pyrrolo[2,3-d]pyrimidin-4-yl)amino]cyclohexyl}-N-[(1S,2R)-2-phenylcyclopropyl]methanesulfonamide.

In one embodiment, the present invention includes compounds or pharmaceutically acceptable salts thereof, having a structure according to formula I, wherein:

$R^1$ is selected from the group consisting of hydrogen and $(C_1-C_6)$alkyl;

$R^2$ is selected from the group consisting of phenyl, phenyl$(C_1-C_6)$alkyl, heterocyclyl, and heterocyclyl$(C_1-C_6)$alkyl; and wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, and aminosulfonyl;

wherein heterocyclyl, wherever it occurs, is optionally substituted with one or more substituents independently selected from the group consisting of halo, $(C_1-C_6)$alkyl, $(C_1-C_6)$alkoxy, and amino; and wherein the $(C_1-C_6)$alkyl in phenyl$(C_1-C_6)$alkyl and heterocyclyl$(C_1-C_6)$alkyl is optionally substituted with one more substituents independently selected from the group consisting of halo and hydroxy; and $R^3$ selected from the group consisting of hydrogen and $(C_1-C_6)$alkyl.

In some embodiments, the present invention includes compounds or pharmaceutically acceptable salts thereof, having a structure according to formula I, wherein:

$R^1$ is selected from the group consisting of hydrogen and $(C_1-C_6)$alkyl;

$R^2$ is selected from the group consisting of phenyl and phenyl$(C_1-C_6)$alkyl; and wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, and aminosulfonyl; and wherein the $(C_1-C_6)$alkyl in phenyl$(C_1-C_6)$alkyl is optionally substituted with one more substituents independently selected from the group consisting of halo and hydroxy; and $R^3$ selected from the group consisting of hydrogen and $(C_1-C_6)$alkyl.

In some embodiments, the present invention includes compounds or pharmaceutically acceptable salts thereof, having a structure according to formula I, wherein:

$R^1$ is selected from the group consisting of hydrogen and $(C_1-C_6)$alkyl;

$R^2$ is selected from the group consisting of phenyl and phenyl$(C_1-C_4)$alkyl;

wherein phenyl, wherever it occurs, is optionally substituted with one or more substituents independently selected from the group consisting of cyano, chloro, fluoro, hydroxy, methyl, trifluoromethyl, cyanomethyl, methoxy, and aminosulfonyl; and wherein the $(C_1-C_4)$alkyl in phenyl$(C_1-C_4)$alkyl is optionally substituted with one more substituents independently selected from the group consisting of fluoro and hydroxy; and $R^3$ is selected from the group consisting of hydrogen and methyl.

In some embodiments, the present invention includes compounds or pharmaceutically acceptable salts thereof, having a structure according to formula I, wherein:

$R^1$ is selected from the group consisting of hydrogen and methyl;

$R^2$ is selected from the group consisting of phenyl and phenyl$(C_1-C_4)$alkyl;

wherein phenyl, wherever it occurs, is optionally substituted with one or more substituents independently selected from the group consisting of cyano, chloro, fluoro, hydroxy, methyl, trifluoromethyl, cyanomethyl, methoxy, and aminosulfonyl; and wherein the $(C_1-C_4)$alkyl in phenyl$(C_1-C_4)$alkyl is optionally substituted with one more substituents independently selected from the group consisting of fluoro and hydroxy; and $R^3$ is selected from the group consisting of hydrogen and methyl.

In one embodiment, the present invention includes compounds or pharmaceutically acceptable salts thereof, selected from the group consisting of 4-(2-{[({trans-4-[methyl(7H-pyrrolo[2,3-d]pyrimidin-4-yl)amino]cyclohexyl}methyl)sulfonyl]amino}ethyl)benzenesulfonamide;

N-[2-(4-hydroxyphenyl)ethyl]-1-{trans-4-[methyl(7H-pyrrolo[2,3-d]pyrimidin-4-yl)amino]cyclohexyl}methanesulfonamide;

N-[2-(2,4-dimethylphenyl)ethyl]-1-{trans-4-[methyl(7H-pyrrolo[2,3-d]pyrimidin-4-yl)amino]cyclohexyl}methanesulfonamide;

N-[2-(2-methoxyphenyl)ethyl]-1-{trans-4-[methyl(7H-pyrrolo[2,3-d]pyrimidin-4-yl)amino]cyclohexyl}methanesulfonamide;

N-(2,2-difluoro-2-phenylethyl)-1-{trans-4-[methyl(7H-pyrrolo[2,3-d]pyrimidin-4-yl)amino]cyclohexyl}methanesulfonamide;

N-[2-(4-methylphenyl)ethyl]-1-{trans-4-[methyl(7H-pyrrolo[2,3-d]pyrimidin-4-yl)amino]cyclohexyl}methanesulfonamide;

N-[2-fluoro-2-(4-fluorophenyl)propyl]-1-{trans-4-[methyl(7H-pyrrolo[2,3-d]pyrimidin-4-yl)amino]cyclohexyl}methanesulfonamide;

N-[2-fluoro-2-(3-fluorophenyl)propyl]-1-{trans-4-[methyl(7H-pyrrolo[2,3-d]pyrimidin-4-yl)amino]cyclohexyl}methanesulfonamide;

N-[2-(3-methoxyphenyl)ethyl]-1-{trans-4-[methyl(7H-pyrrolo[2,3-d]pyrimidin-4-yl)amino]cyclohexyl}methanesulfonamide;

N-[2-fluoro-2-(4-fluorophenyl)ethyl]-1-{trans-4-[methyl(7H-pyrrolo[2,3-d]pyrimidin-4-yl)amino]cyclohexyl}methanesulfonamide;

1-{trans-4-[methyl(7H-pyrrolo[2,3-d]pyrimidin-4-yl)amino]cyclohexyl}-N-{2-[4-(trifluoromethyl)phenyl]ethyl}methanesulfonamide;

N-{2-[2-fluoro-4-(trifluoromethyl)phenyl]ethyl}-1-{trans-4-[methyl(7H-pyrrolo[2,3-d]pyrimidin-4-yl)amino]cyclohexyl}methanesulfonamide;

1-{trans-4-[methyl(7H-pyrrolo[2,3-d]pyrimidin-4-yl)amino]cyclohexyl}-N-(2-phenylethyl)methanesulfonamide;

N-benzyl-1-{trans-4-[methyl(7H-pyrrolo[2,3-d]pyrimidin-4-yl)amino]cyclohexyl}methanesulfonamide;

N-(4-methoxybenzyl)-1-{trans-4-[methyl(7H-pyrrolo[2,3-d]pyrimidin-4-yl)amino]cyclohexyl}methanesulfonamide;

N-[4-(cyanomethyl)phenyl]-1-{trans-4-[methyl(7H-pyrrolo[2,3-d]pyrimidin-4-yl)amino]cyclohexyl}methanesulfonamide;

N-(4-cyanophenyl)-1-{trans-4-[methyl(7H-pyrrolo[2,3-d]pyrimidin-4-yl)amino]cyclohexyl}methanesulfonamide;

N-[2-(4-chlorophenyl)ethyl]-1-{trans-4-[methyl(7H-pyrrolo[2,3-d]pyrimidin-4-yl)amino]cyclohexyl}methanesulfonamide;

N-[2-(2-fluorophenyl)ethyl]-1-{trans-4-[methyl(7H-pyrrolo[2,3-d]pyrimidin-4-yl)amino]cyclohexyl}methanesulfonamide;

N-[2-(3-fluorophenyl)ethyl]-1-{trans-4-[methyl(7H-pyrrolo[2,3-d]pyrimidin-4-yl)amino]cyclohexyl}methanesulfonamide;

N-[2-(3-chlorophenyl)ethyl]-1-{trans-4-[methyl(7H-pyrrolo[2,3-d]pyrimidin-4-yl)amino]cyclohexyl}methanesulfonamide;

N-[2-(2-fluoro-4-isopropylphenyl)ethyl]-1-{trans-4-[methyl(7H-pyrrolo[2,3-d]pyrimidin-4-yl)amino]cyclohexyl}methanesulfonamide;

N-[2-(3,4-difluorophenyl)-2-hydroxyethyl]-1-{trans-4-[methyl(7H-pyrrolo[2,3-d]pyrimidin-4-yl)amino]cyclohexyl}methanesulfonamide;

N-[3-(2-methoxyphenyl)propyl]-1-{trans-4-[methyl(7H-pyrrolo[2,3-d]pyrimidin-4-yl)amino]cyclohexyl}methanesulfonamide;

N-[2-(3,4-dichlorophenyl)ethyl]-1-{trans-4-[methyl(7H-pyrrolo[2,3-d]pyrimidin-4-yl)amino]cyclohexyl}methanesulfonamide;

1-{cis-4-[methyl(7H-pyrrolo[2,3-d]pyrimidin-4-yl)amino]cyclohexyl}-N-(2-phenylethyl)methanesulfonamide;

N-benzyl-1-{cis-4-[methyl(7H-pyrrolo[2,3-d]pyrimidin-4-yl)amino]cyclohexyl}methanesulfonamide; and N-(4-methoxybenzyl)-1-{cis-4-[methyl(7H-pyrrolo[2,3-d]pyrimidin-4-yl)amino]cyclohexyl}methanesulfonamide.

In some embodiments, the present invention includes compounds or pharmaceutically acceptable salts thereof, having a structure according to formula I, wherein:

$R^1$ is selected from the group consisting of hydrogen and $(C_1-C_6)$alkyl;

$R^2$ is selected from the group consisting of heterocyclyl and heterocyclyl$(C_1-C_6)$alkyl; and wherein heterocyclyl, wherever it occurs, is optionally substituted with one or more substituents independently selected from the group consisting of halo, $(C_1-C_6)$alkyl, $(C_1-C_6)$alkoxy, and amino; and wherein the $(C_1-C_6)$alkyl in heterocyclyl$(C_1-C_6)$alkyl is optionally substituted with one more substituents independently, selected from the group consisting of halo and hydroxy; and $R^3$ selected from the group consisting of hydrogen and $(C_1-C_6)$alkyl.

In some embodiments, the present invention includes compounds or pharmaceutically acceptable salts thereof, having a structure according to formula I, wherein:

$R^1$ is selected from the group consisting of hydrogen and $(C_1-C_6)$alkyl;

$R^2$ is selected from the group consisting of 3-12 membered ring heterocyclyl and 3-12 membered ring heterocyclyl$(C_1-C_6)$alkyl; and wherein heterocyclyl, wherever it occurs, is optionally substituted with one or more substituents independently selected from the group consisting of halo, $(C_1-C_6)$alkyl, $(C_1-C_6)$alkoxy, and amino; and wherein the $(C_1-C_6)$alkyl in heterocyclyl$(C_1-C_6)$alkyl is optionally substituted with one more substituents independently selected from the group consisting of halo and hydroxy; and $R^3$ selected from the group consisting of hydrogen and $(C_1-C_6)$alkyl.

In some embodiments, the present invention includes compounds or pharmaceutically acceptable salts thereof, having a structure according to formula I, wherein:

$R^1$ is selected from the group consisting of hydrogen and $(C_1-C_6)$alkyl;

$R^2$ is selected from the group consisting of indolyl, indazolyl, pyridinyl, pyrimidinyl, pyrazinyl, pyrazolyl, 3,4-dihydro-2H-benzo[b][1,4]dioxepinyl, tetrahydrofuranyl, indolyl$(C_1-C_6)$alkyl, indazolyl$(C_1-C_6)$alkyl, pyridinyl$(C_1-C_6)$alkyl, pyrimidinyl$(C_1-C_6)$alkyl, pyrazinyl$(C_1-C_6)$alkyl, pyrazolyl$(C_1-C_6)$alkyl, 3,4-dihydro-2H-benzo[b][1,4]dioxepinyl$(C_1-C_6)$alkyl, and tetrahydrofuranyl$(C_1-C_6)$alkyl; and wherein indolyl, indazolyl, pyridinyl, pyrimidinyl, pyrazinyl, pyrazolyl, 3,4-dihydro-2H-benzo[b][1,4]dioxepinyl, tetrahydrofuranyl are optionally substituted with one or more substituents independently selected from the group consisting of halo, $(C_1-C_6)$alkyl, $(C_1-C_6)$alkoxy, and amino; and wherein the $(C_1-C_6)$alkyl in indolyl$(C_1-C_6)$alkyl, indazolyl$(C_1-C_6)$alkyl, pyridinyl$(C_1-C_6)$alkyl, pyrimidinyl$(C_1-C_6)$alkyl, pyrazinyl$(C_1-C_6)$alkyl, pyrazolyl$(C_1-C_6)$alkyl, 3,4-dihydro-2H-benzo[b][1,4]dioxepinyl$(C_1-C_6)$alkyl, and tetrahydrofuranyl$(C_1-C_6)$alkyl is optionally substituted with one more substituents independently selected from the group consisting of halo and hydroxy; and $R^3$ selected from the group consisting of hydrogen and $(C_1-C_6)$alkyl.

In some embodiments, the present invention includes compounds or pharmaceutically acceptable salts thereof, having a structure according to formula I, wherein:

$R^1$ is selected from the group consisting of hydrogen and $(C_1-C_6)$alkyl;

$R^2$ is selected from the group consisting of indolyl, indazolyl, pyridinyl, pyrazolyl, 3,4-dihydro-2H-benzo[b][1,4]dioxepinyl, indolylmethyl, pyridinylmethyl, pyrimidinylmethyl, pyrazinylmethyl, pyrazolylmethyl, tetrahydrofuranylmethyl, and pyridinylethyl; and wherein indolyl, indazolyl, pyridinyl, pyrimidinyl, pyrazinyl, pyrazolyl, 3,4-dihydro-2H-benzo[b][1,4]dioxepinyl, and tetrahydrofuranyl are optionally substituted with one or more substituents independently selected from the group consisting of halo, ($C_1$-$C_6$)alkyl, ($C_1$-$C_6$)alkoxy, and amino; and $R^3$ selected from the group consisting of hydrogen and ($C_1$-$C_6$)alkyl.

In some embodiments, the present invention includes compounds or pharmaceutically acceptable salts thereof, having a structure according to formula I, wherein:

$R^1$ is selected from the group consisting of hydrogen and methyl;

$R^2$ is selected from the group consisting of indolyl, indazolyl, pyridinyl, pyrazolyl, 3,4-dihydro-2H-benzo[b][1,4]dioxepinyl, indolylmethyl, pyridinylmethyl, pyrimidinylmethyl, pyrazinylmethyl, pyrazolylmethyl, tetrahydrofuranylmethyl, and pyridinylethyl;

wherein indolyl, indazolyl, pyridinyl, pyrimidinyl, pyrazinyl, pyrazolyl, 3,4-dihydro-2H-benzo[b][1,4]dioxepinyl, and tetrahydrofuranyl, are optionally substituted with one or more substituents independently selected from the group consisting of chloro, methyl, methoxy, and amino; and $R^3$ selected from the group consisting of hydrogen and methyl.

In one embodiment, the present invention includes compounds or pharmaceutically acceptable salts thereof, selected from the group consisting of 1-{trans-4-[methyl(7H-pyrrolo[2,3-d]pyrimidin-4-yl)amino]cyclohexyl}-N-(pyridin-3-ylmethyl)methanesulfonamide;

1-{trans-4-[methyl(7H-pyrrolo[2,3-d]pyrimidin-4-yl)amino]cyclohexyl}-N-1H-pyrazol-5-ylmethanesulfonamide;

N-(5-methyl-1H-pyrazol-3-yl)-1-{trans-4-[methyl(7H-pyrrolo[2,3-d]pyrimidin-4-yl)amino]cyclohexyl}methanesulfonamide;

N-1H-indol-5-yl-1-{trans-4-[methyl(7H-pyrrolo[2,3-d]pyrimidin-4-yl)amino]cyclohexyl}methanesulfonamide;

N-(6-chloropyridin-3-yl)-1-{trans-4-[methyl(7H-pyrrolo[2,3-d]pyrimidin-4-yl)amino]cyclohexyl}methanesulfonamide;

N-1H-indazol-5-yl-1-{trans-4-[methyl(7H-pyrrolo[2,3-d]pyrimidin-4-yl)amino]cyclohexyl}methanesulfonamide;

N-(3,4-dihydro-2H-1,5-benzodioxepin-7-yl)-1-{trans-4-[methyl(7H-pyrrolo[2,3-d]pyrimidin-4-yl)amino]cyclohexyl}methanesulfonamide;

N-(6-methoxypyridin-3-yl)-1-{trans-4-[methyl(7H-pyrrolo[2,3-d]pyrimidin-4-yl)amino]cyclohexyl}methanesulfonamide;

N-(6-methylpyridin-3-yl)-1-{trans-4-[methyl(7H-pyrrolo[2,3-d]pyrimidin-4-yl)amino]cyclohexyl}methanesulfonamide;

N-[(2-methyl-1H-indol-5-yl)methyl]-1-{trans-4-[methyl(7H-pyrrolo[2,3-d]pyrimidin-4-yl)amino]cyclohexyl}methanesulfonamide;

N-[(5-methylpyrazin-2-yl)methyl]-1-{trans-4-[methyl(7H-pyrrolo[2,3-d]pyrimidin-4-yl)amino]cyclohexyl}methanesulfonamide;

1-{trans-4-[methyl(7H-pyrrolo[2,3-d]pyrimidin-4-yl)amino]cyclohexyl}-N-[(2R)-tetrahydrofuran-2-ylmethyl]methanesulfonamide;

N-[2-(6-methylpyridin-2-yl)ethyl]-1-{trans-4-[methyl(7H-pyrrolo[2,3-d]pyrimidin-4-yl)amino]cyclohexyl}methanesulfonamide;

N-[(4,6-dimethylpyrimidin-2-yl)methyl]-1-{trans-4-[methyl(7H-pyrrolo[2,3-d]pyrimidin-4-yl)amino]cyclohexyl}methanesulfonamide; and N-[(1,3-dimethyl-1H-pyrazol-4-yl)methyl]-1-{trans-4-[methyl(7H-pyrrolo[2,3-d]pyrimidin-4-yl)amino]cyclohexyl}methanesulfonamide.

In one embodiment, the present invention includes a pharmaceutical composition comprising a compound of Formula I or a pharmaceutically acceptable salt thereof.

In one embodiment, the present invention includes a method for the treatment of a Janus Kinase mediated condition in a subject in need of such treatment, wherein the method comprises administering to the subject an amount of a compound of Formula I or a pharmaceutically acceptable salt thereof, wherein the amount of the compound is effective for the treatment of the Janus Kinase mediated condition.

In one embodiment, the Janus Kinase mediated condition is Alzheimer's disease, arthritis, autoimmune thyroid disorders, cancer, diabetes, leukemia, T-cell prolymphocytic leukemia, lymphoma, myeoproliferation disorders, lupus, multiple myeloma, multiple sclerosis, osteoarthritis, sepsis, prostate cancer, T-cell autoimmune disease, inflammatory diseases, chronic and acute allograft transplant rejection, bone marrow transplant, stroke, asthma, chronic obstructive pulmonary disease, allergy, bronchitis, viral diseases, or Type I diabetes and complications from diabetes.

In one embodiment, the Janus Kinase mediated condition is selected from the group consisting of asthma, Crohn's disease, dry eye, uveitis, inflammatory bowel disease, organ transplant rejection, psoriasis, rheumatoid arthritis, psoriatic arthritis, ankylosing spondylitis and ulcerative colitis.

Pharmaceutically acceptable salts of the compounds of formula I include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts. For a review on suitable salts, see *Handbook of Pharmaceutical Salts Properties, Selection, and Use* by Stahl and Wermuth (Wiley-VCH, 2002).

Pharmaceutically acceptable salts of compounds of formula I may be prepared by one or more of three methods: (i) by reacting the compound of formula I with the desired acid or base; (ii) by removing an acid- or base-labile protecting group from a suitable precursor of the compound of formula I or by ring-opening a suitable cyclic precursor, for example, a lactone or lactam, using the desired acid or base; or (iii) by converting one salt of the compound of formula I to another by reaction with an appropriate acid or base or by means of a suitable ion exchange column. All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula I include references to salts, solvates, multi-component complexes and liquid crystals thereof and to solvates, multi-component complexes and liquid crystals of salts thereof.

The compounds of the invention include compounds of formula I as hereinbefore defined, including all polymorphs and crystal habits thereof, prodrugs and isomers thereof (including optical, geometric and tautomeric isomers) as hereinafter defined and isotopically-labeled compounds of formula I.

As indicated, so-called 'prodrugs' of the compounds of formula I are also within the scope of the invention. Thus certain derivatives of compounds of formula I which may have little or no pharmacological activity themselves can, when administered into or onto the body, be converted into compounds of formula I having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula I with certain moieties known to those skilled in the art as 'pro-moieties' as described, for example, in *Design of Prodrugs* by H. Bundgaard (Elsevier, 1985).

Some examples of prodrugs in accordance with the invention include: (i) where the compound of formula I contains a carboxylic acid functionality (—COOH), an ester thereof, for example, a compound wherein the hydrogen of the carboxylic acid functionality of the compound of formula (I) is replaced by $(C_1-C_8)$alkyl; (ii) where the compound of formula I contains an alcohol functionality (—OH), an ether thereof, for example, a compound wherein the hydrogen of the alcohol functionality of the compound of formula I is replaced by $(C_1-C_6)$alkanoyloxymethyl; and (iii) where the compound of formula I contains a primary or secondary amino functionality ($-NH_2$ or —NHR where R≠H), an amide thereof, for example, a compound wherein, as the case may be, one or both hydrogens of the amino functionality of the compound of formula I is/are replaced by $(C_1-C_{10})$alkanoyl. Further examples of replacement groups in accordance with the foregoing examples and examples of other prodrug types may be found in the aforementioned references. Moreover, certain compounds of formula I may themselves act as prodrugs of other compounds of formula I.

Also included within the scope of the invention are metabolites of compounds of formula I, that is, compounds formed in vivo upon administration of the drug. Some examples of metabolites in accordance with the invention include: (i) where the compound of formula I contains a methyl group, an hydroxymethyl derivative thereof ($-CH_3 \rightarrow -CH_2OH$): (ii) where the compound of formula I contains an alkoxy group, an hydroxy derivative thereof (—OR→—OH); (iii) where the compound of formula I contains a tertiary amino group, a secondary amino derivative thereof (—$Na^1R^2$→—$NHR^1$ or —$NHR^2$); (iv) where the compound of formula I contains a secondary amino group, a primary derivative thereof (—$NHR^1$→—$NH_2$); (v) where the compound of formula I contains a phenyl moiety, a phenol derivative thereof (-Ph→-PhOH); and (vi) where the compound of formula I contains an amide group, a carboxylic acid derivative thereof (—$CONH_2$→COOH).

Compounds of formula I containing one or more asymmetric carbon atoms can exist as two or more stereoisomers. Where a compound of formula I contains an alkenyl or alkenylene group, geometric cis/trans (or Z/E) isomers are possible. Where, structural isomers are interconvertible via a low energy barrier, tautomeric isomerism ('tautomerism') can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, a base or acid, such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula I wherein one or more atoms are replaced by atoms having the same atomic number, but an atomic mass or mass number different from the atomic mass or mass number which predominates in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{18}N$, oxygen, such as $^{15}O$, $^{17}O$ and $^{18}O$, phosphorus, such as $^{32}P$, and sulphur, such as $^{35}S$ Certain isotopically-labelled compounds of formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds of formula I as hereinbefore defined, all salts, solvates and complexes thereof and all solvates and complexes of salts thereof as defined hereinbefore for compounds of formula I. The invention includes all polymorphs of the aforementioned species and crystal habits thereof.

When preparing compounds of formula I in accordance with the invention, it is open to a person skilled in the art to routinely select the form of compound of formula I which provides the best combination of features for this purpose. Such features include the melting point, solubility, processability and yield of the intermediate form and the resulting ease with which the product may be purified on isolation.

Pharmaceutical Compositions

Also provided are compositions which can be prepared by mixing one or more compounds described herein, or pharmaceutically acceptable salts or tautomers thereof, with pharmaceutically acceptable carriers, excipients, binders, diluents or the like, to treat or ameliorate a variety of JAK related conditions. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, transmucosal administration, rectal administration, topical administration or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments can be added for identification. Tablets and pills can be further treated with suitable coating materials known in the art.

Liquid dosage forms for oral administration can be in the form of pharmaceutically acceptable emulsions, syrups, elixirs, suspensions, slurries and solutions, which can contain an inactive diluent, such as water. Pharmaceutical formulations can be prepared as liquid suspensions or solutions using a sterile liquid, such as, but not limited to, an oil, water, an alcohol, and combinations of these. Pharmaceutically suitable surfactants, suspending agents, emulsifying agents, can be added for oral or parenteral administration.

As noted above, suspensions can include oils. Such oils include, but are not limited to, peanut oil, sesame oil, cottonseed oil, corn oil, olive oil and mixtures of oils. Suspension preparation can also contain esters of fatty acids such as ethyl oleate, isopropyl myristate, fatty acid glycerides and acetylated fatty acid glycerides. Suspension formulations can include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water can also be used in suspension formulations.

The compounds may also be administered topically, (intra) dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated-see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

For nasal administration, the pharmaceutical formulations can be a spray or aerosol containing and appropriate solvents and optionally other compounds such as, but not limited to, stabilizers, antimicrobial agents, antioxidants, pH modifiers, surfactants, bioavailablity modifiers and combinations of these. A propellant for an aerosol formulation can include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Generally, the oil or fatty acid is non-volatile, including natural or synthetic oils, fatty acids, mono-, di- or tri-glycerides.

For injection, the pharmaceutical formulation can be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

For rectal administration, the pharmaceutical formulations can be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils can also be employed in the preparation of formulations of the soft gelatin type, and suppositories. Water, saline, aqueous dextrose and related sugar solutions, and glycerols can be employed in the preparation of suspension formulations which can also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991).

The formulations of the invention can be designed for to be short-acting, fast-releasing, long-acting, and sustained-releasing. Thus, the pharmaceutical formulations can also be formulated for controlled release or for slow release.

The instant compositions can also comprise, for example, micelles or liposomes, or some other encapsulated form, or can be administered in an extended release form to provide a prolonged storage and/or delivery effect. Therefore, the pharmaceutical formulations can be compressed into pellets or cylinders and implanted intramuscularly or subcutaneously as depot injections or as implants such as stents. Such implants can employ known materials such as silicones and biodegradable polymers.

The compositions may contain, for example, from about 0.1% by weight, to about 90% or more by weight, of the active material, depending on the method of administration. Where the compositions comprise dosage units, each unit can contain, for example, from about 0.1 to 500 mg or more of the active ingredient. The dosage as employed for adult human treatment can range, for example, from about 0.1 to 1000 mg per day, depending on the route and frequency of administration.

Specific dosages can be adjusted depending on conditions of the JAK related condition, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention. Generally, the total daily dose can typically range from about 1 mg/kg/day to about 500 mg/kg/day in single or in divided doses. Typically, dosages for humans can range from about 5 mg to about 100 mg per day, in a single or multiple doses.

A therapeutically effective dose or amount can vary depending upon the route of administration and dosage form. Some compositions of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ can be determined by standard pharmaceutical procedures in animal cell cultures or experimental models.

Pharmaceutical preparations of the JAK inhibitors, such as the compound (I), either from alone or in combination with one or more additional agents which may include but are not limited to cyclosporin A, rapamycin, tacrolimus, sirolimus, everolimus, micophenolate (e.g. Cellcept®, Myfortic®, etc.), azathioprine, brequinar, deoxyspergualin, leflunomide, sphingosine-1-phosphate receptor agonist (e.g. fingolimod, KRP-203, etc.), LEA-29Y, anti-IL-2 receptor antibody (e.g. daclizumab, etc.), anti-CD3 antibody (e.g. OKT3, etc.), Anti-T cell immunogloblin (e.g. AtGam, etc.), aspirin, CD28-B7 blocking molecules (e.g. Belatacept, Abatacept, etc.), CD40-CD154 blocking molecules (e.g. Anti-CD40 antibody, etc.), protein kinase C inhibitor (e.g. AEB-071, etc.), acetaminophen, ibuprofen, naproxen, piroxicam, methotrexate, an anti inflammatory steroid (e.g. prednisolone or dexamethasone) or those disclosed in PCT application no. PCT/IB2007/002468. These combinations can be administered as part of the same or separate dosage forms, via the same or different routes of administration, and on the same or different administration schedules according to standard pharmaceutical practice.

Also provided is an article of manufacture comprising a pharmaceutical composition comprising a provided compound contained within a packaging material and a label or package insert which indicates that said pharmaceutical composition can be used for treating a JAK related condition, as described herein.

Methods of Treatment

In one embodiment, the invention provides methods of treating or preventing a condition associated with JAK in a subject, such as a mammal, i.e., a human or non-human mammal, comprising administering an effective amount of one or more compounds described herein to the subject. The JAK associated condition can be related to JAK1, JAK2, JAK3, and/or Tyk2. Suitable non-human subjects that can be treated include domestic or wild animals, companion animals, such as dogs, cats and the like; livestock, including horses, cows and other ruminants, pigs, poultry, rabbits and the like; primates, for example monkeys, such as macaques including rhesus monkeys and cynomolgus (also known as crab-eating or long-tailed) monkeys, marmosets, tamarins and the like, apes, including chimpanzees and orangutans; and rodents, such as rats, mice, gerbils, guinea pigs and the like. In one embodiment, the compound is administered in a pharmaceutically acceptable form, optionally in a pharmaceutically acceptable carrier.

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), Mol. Med. 5:432:456 and Seidel et al., (2000), Oncogene 19:2645-2656.

JAK3 in particular has been implicated in a variety of biological processes. For example, the proliferation and survival of murine mast cells induced by IL-4 and IL-9 have been shown to be dependent on JAK3 and gamma chain-signaling. Suzuki et al., (2000), Blood 96:2172-2180. JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating conditions where the function of lymphocytes, macrophages, or mast cells is involved (Kudlacz et al., (2004) Am. J. Transplant 4:51-57; Changelian (2003) Science 302:875-878).

Conditions in which targeting of the JAK pathway or modulation of the JAK kinases, particularly JAK3, are contemplated to be therapeutically useful include, arthritis, asthma, autoimmune diseases, cancers or tumors, diabetes, certain eye diseases, disorders or conditions, inflammation, intestinal inflammations, allergies or conditions, neurodegenerative diseases, psoriasis, transplant rejection, and viral infection. Conditions which can benefit for inhibition of JAK3 are discussed in greater detail below.

Accordingly, the described compounds, pharmaceutically acceptable salts and pharmaceutical compositions can be used to treat a variety of conditions such as the following.

In some embodiments, the methods and compositions of the present invention encompass the treatment of the connective tissue and joint disorders such as arthritis, rheumatoid arthritis, ankylosing spondylitis, fibromyalgia, spondyloarthopathies, gouty arthritis, lumbar spondylarthrosis, carpal tunnel syndrome, psoriatic arthritis, sclerodoma, canine hip dysplasia, systemic lupus erythematosus, juvenile arthritis, osteoarthritis, tendonitis and bursitis.

In other embodiments, the methods and compositions of the present invention encompass the treatment of neuroinflammation and neurodegenerative disorders such as Alzheimer's disease, multiple sclerosis (MS), Parkinson's disease, motor neuron disease, amyotrophic lateral sclerosis, Huntington's disease, cerebral ischemia, neurodegenerative disease caused by traumatic injury, the neurological complications of AIDS, spinal cord injury, and some peripheral neuropathies and neurodegenerative disorders.

In other embodiments, the methods and compositions of the present invention encompass the treatment of autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be O-cell (humoral) based or T-cell based, including Cogan's syndrome, Wegener's granulomatosis, autoimmune alopecia, and thyroiditis.

In other embodiments, the methods and compositions of the present invention encompass the treatment of diabetes, including Type I diabetes, juvenile onset diabetes and complications from diabetes.

In other embodiments, the methods and compositions of the present invention encompass the treatment of cancers or tumors, including alimentary/gastrointestinal tract cancer, colon cancer, liver cancer, skin cancer, breast cancer, ovarian cancer, prostate cancer, lymphoma, leukemia, including acute myelogenous leukemia and chronic myelogenous leukemia, T-cell prolymphocytic leukemia, kidney cancer, lung cancer, muscle cancer, bone cancer, bladder cancer, brain cancer, metastatic melanoma, Kaposi's sarcoma, myelomas including multiple myeloma, myeloproliferative disorders, proliferative diabetic retinopathy, and angiogenic-associated disorders including solid tumors In other embodiments, the methods and compositions of the present invention encompass the treatment of respiratory disorders such as asthma, bronchitis, chronic obstructive pulmonary disease (COPD), airway hyper-responsiveness, bronchial asthma, allergic asthma, intrinsic asthma, extrinsic asthma, dust asthma, cystic fibrosis, pulmonary edema, pulmonary embolism, pneumonia, pulmonary sarcoisosis, silicosis, pulmonary fibrosis, respiratory failure, acute respiratory distress syndrome and emphysema.

In other embodiments, the methods and compositions of the present invention encompass the treatment of viral infections such as Epstein Barr Virus, Hepatitis B, Hepatitis C, HIV, HTLV1, Varicella-Zoster Virus, and Human Papilloma Virus.

In other embodiments, the methods and compositions of the present invention encompass the treatment of the dermatological disorders such as acne, psoriasis, eczema, burns, poison ivy, poison oak, dermatitis, atopic dermatitis, pruritus and scleroderma.

In other embodiments, the methods and compositions of the present invention encompass the treatment of the allergic reactions, allergic dermatitis, recurrent airway obstruction, heaves, inflammatory airway disease and otitis.

In other embodiments, the methods and compositions of the present invention encompass the treatment of the surgical disorders such as pain and swelling following surgery, infection following surgery and inflammation following surgery.

In other embodiments, the methods and compositions of the present invention encompass the treatment of transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, chronic and acute allograft transplant rejection and xeno transplantion.

In other embodiments, the methods and compositions of the present invention encompass the treatment of the gastrointestinal disorders such as inflammatory bowel disease, irritable bowel syndrome, Crohn's disease, gastritis, irritable bowel syndrome, diarrhea, constipation, dysentery, ulcerative colitis, gastric esophageal reflux, gastric ulcers, gastric varices, ulcers, heartburn, coeliac diseases, proctitis, eosinophilic gastroenteritis, and mastocytosis.

In other embodiments, the methods and compositions of the present invention encompass the treatment of the ophthalmic disorders such as retinopathies, uveitis, ocular photophobia, acute injury to the eye tissue, conjunctivitis, age-related macular degeneration diabetic retinopathy, detached retina, glaucoma, vitelliform macular dystrophy type 2, gyrate atrophy of the choroid and retina, conjunctivitis, corneal infection, fuchs' dystrophy, iridocorneal endothelial syndrome, keratoconus, lattice dystrophy, map-dot-fingerprint dystrophy, ocular herpes, pterygium, myopia, hyperopia, cataracts, keratoconjunctivitis, vernal conjunctivitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization.

In other embodiments, the methods and compositions of the present invention encompass the treatment of pain, including but not limited to chronic pain, acute pain, joint pain, nociceptive pain, neuropathic pain, allodynia, hyperalgesia, burn pain, menstrual cramps, kidney stones, headache, migraine headache, sinus headaches, tension headaches, dental pain, myasthenia gravis, multiple sclerosis, sarcoidosis, Behcet's syndrome, myositis, polymyositis, gingivitis, hypersensitivity, swelling occurring after injury, closed head injury, endometriosis, vasculitis, sepsis, glutamate neurotoxicity or hypoxia; ischemic/reperfusion injury in stroke, myocardial ischemica, renal ischemia, heart attacks, stroke, cardiac hypertrophy, coronary artery disease, atherosclerosis and arteriosclerosis, organ hypoxia, and platelet aggregation, stroke, and the like.

Additional examples of the diseases and disorders associated with JAK inhibition and that can be treated include those disclosed in WO 2007/077949, U.S. patent publication nos. US 2007/0259904, US 2007/0207995, US 2007/0203162, and US 2006/0293311.

The compounds described herein can also be used prophylactically for the prevention of organ transplant rejection. For example, the compounds and pharmaceutical formulations of the present invention can be administered before, during, and/or after a surgical procedure, such as an organ transplant surgery.

Another embodiment provides a method of inhibiting a JAK enzyme, including JAK-1, JAK-2, JAK-3 and/or Tyk-2, that includes contacting the JAK enzyme with either a non-therapeutic amount or a therapeutically effective amount of one or more of the present compounds. Such methods can occur in vivo or in vitro. In vitro contact can involve a screening assay to determine the efficacy of the one or more compounds against a selected enzyme at various amounts or concentrations. In vivo contact with a therapeutically effective amount of the one or more compounds can involve treatment of a described condition or prophylaxis of organ transplant rejection in the animal in which the contact occurs. The effect of the one or more compounds on the JAK enzyme and/or host animal can also be determined or measured. Methods for determining JAK activity include those described in the Examples as well as those disclosed in WO 99/65908, WO 99/65909, WO 01/42246, WO 02/00661, WO 02/096909, WO 2004/046112 or WO 2007/012953.

Chemical Synthesis

Representative procedures for the preparation of compounds of the invention are outlined below in the Schemes. The starting materials can be purchased or prepared using methods known to those skilled in the art. Similarly, the preparation of the various intermediates can be achieved using methods known in the art. The starting materials may be varied and additional steps employed to produce compounds encompassed by the invention, as demonstrated by the examples below. In addition, different solvents and reagents can typically be used to achieve the above transformations. Furthermore, in certain situations, it may be advantageous to alter the order in which the reactions are performed. Protection of reactive groups may also be necessary to achieve the above transformations. In general, the need for protecting groups, as well as the conditions necessary to attach and remove such groups, will be apparent to those skilled in the art of organic synthesis. When a protecting group is employed, deprotection will generally be required. Suitable protecting groups and methodology for protection and deprotection such as those described in *Protecting Groups in Organic Synthesis* by Greene and Wuts are known and appreciated in the art.

The compounds described herein can be synthesized as set forth in the examples of the present application.

General Synthetic Procedure 1

The compounds described herein can also be synthesized according to the following general Scheme I:

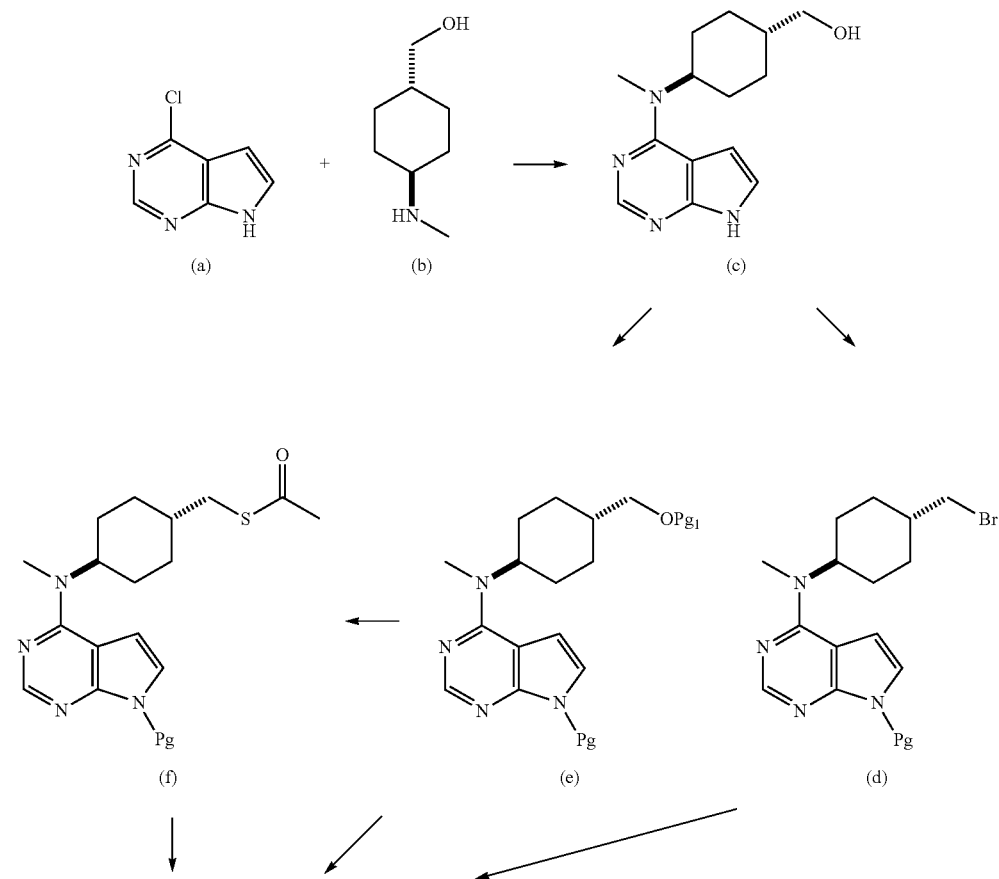

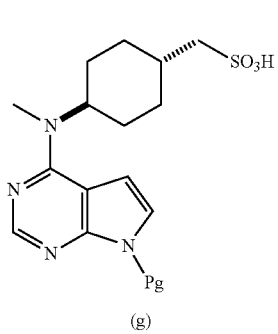 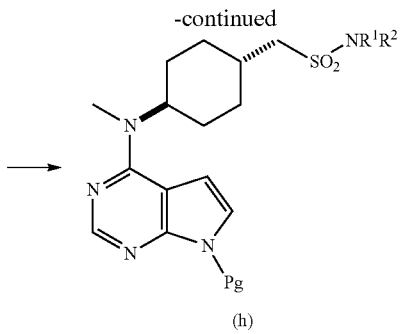 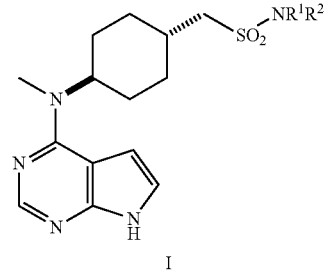

In some synthetic methods, functional groups may need to be protected and deprotected during, synthesis of a compound of the invention. In the present application protecting groups are indicated by the letters. Pg alone or with a numerical designation, such as Pg or Pg1. Those skilled in the art recognize that protection and deprotection of compounds can be achieved by conventional methods, for example as described in "Protective Groups in Organic Synthesis" by T W Greene and P G M Wuts, John Wiley & Sons Inc (1999), and references therein.

In Scheme I, 4-Chloro-7H-pyrrolo[2,3-d]pyrimidine (a) can be obtained Id commercially (GL Synthesis, Inc., Worchester, Mass.). 4-[(Methylamino)-cyclohexyl]-methanol (b) can be obtained from the corresponding carboxylic acid, 4-[(tert-butoxy-carbonyl)amino]cyclohexanecarboxylic acid, by treatment with a reducing agent, such as lithium aluminium hydride, which can occur in an aprotic, anhydrous solvent, such as tetrahydrofuran. Conversion of (a) to (b) can occur at a range of temperatures, typically between about 0 to 60° C. and completion of the reaction can take up to several hours.

As shown in Scheme I, a compound of structure (c) can be synthesized by the reaction of 4-chloro-7H-pyrrolo[2,3-d]pyrimidine (a) with 4-[(methylamino)-cyclohexyl]methanol (b) in a suitable solvent, such as a polar, aprotic solvent, for example N,N-dimethylformamide, aqueous dioxane and/or dimethylsulfoxide, in the presence of a suitable base, such as triethylamine and/or potassium carbonate. This reaction can occur at elevated temperatures up to about 90° C. and the reaction can occur for up to a few hours or longer.

A compound of structure (d) can be synthesized from a compound of structure (c) as shown above. For example, a compound of structure (d) can be synthesized by using a brominating reagent, such as thionyl bromide or phosphorous tribromide, in a polar, aprotic solvent, such as methylene chloride, to afford an unprotected cyclohexylmethylbromide, and which can give the protected compound of structure (d) by addition of a suitable protecting reagent, such as tosyl chloride.

A compound of structure (e) can be prepared by using protection processes from a compound of structure (c). For example, when Pg and Pg1 are both tosyl, (e) can be prepared in a one step reaction upon treatment of the unprotected compound of structure (c) with tosyl chloride in the presence of a polar, aprotic solvent, such as methylene chloride, a catalyst, such as DMAP, and a weak base, such as triethylamine.

A compound of structure (f) can be synthesized from a compound of structure (e) by S-alkylation using a suitable nucleophile. Thus compounds of structure (e), wherein the protecting group (Pg1)) is a suitable hydroxyl protecting group such as tosyl or mesyl, can be reacted with potassium thioacetate in a polar solvent, such as dimethylsulfoxide or N-methylpyrrolidine, to give compounds of structure (f). This reaction can occur at elevated temperatures up to 75° C. and can take place for up to 2 hours or longer.

A compound of structure (g) can be synthesized by an oxidation procedure from the compound of formula (f). The oxidation step is not critical to the present scheme, and many oxidizing conditions are known to those skilled in the art, for example those described in "Handbook of Reagents for Organic Synthesis—Oxidising and Reducing Agents" edited by S. D. Burke and R. L. Danheiser. In some embodiments, a compound of structure (f), optionally wetted with water, can be treated with formic acid followed by slow addition of hydrogen peroxide. Such a reaction can occur with stirring at room temperature, for a time up to about 15 hours or more, to give a compound of structure (g). Alternatively, Oxone® (DuPont) may be employed in a polar solvent such as acetic acid. In one embodiment, the reaction is performed in the presence of potassium acetate and the potassium salt of the compound of formula (g) is produced.

A compound of structure (g) can be synthesized directly from a compound of structure (e) upon treatment with a suitable sulfur nucleophile, such as sodium sulfite, in a polar solvent. Alternatively, a compound of structure (g) can be synthesized from a compound of structure (d) upon nucleophilic substitution with sodium sulfite.

Treatment of sulphonic acids of formula (g) with a chlorinating agent, such as thionyl chloride, in a polar, aprotic solvent, such as methylene chloride, with a polar cosolvent, such as N,N-dimethylformamide, can provide the appropriate chlorinated compounds. This reaction can occur under reflux conditions. The chlorinated compound can then react in an aprotic, anhydrous solvent, such as tetrahydrofuran, with a suitable amine, which can be in neat, gaseous form, or dissolved in an aprotic, anhydrous solvent such as tetrahydrofuran, to produce a compound of structure (h). In some embodiments, this reaction can occur at room temperature. Optionally an anhydrous, weak base, such as triethylamine, may be used to mop up hydrochloric acid generated in the reaction.

Compounds of formula Ia of the present invention can be prepared from compounds of formula (h), wherein Pg is a suitable protecting group, by deprotection procedures known to those skilled in the art. For example, when the protecting group (Pg) is tosyl, suitable deprotection conditions involve reaction with a base, such as lithium hydroxide or potassium hydroxide in a protic solvent such as methanol or isopropanol and optionally miscible cosolvents such as tetrahydrofuran and water. This deprotection reaction can occur at about room temperature for several hours or more and thereby produce the deprotected amine of formula Ia.

General Synthetic Procedure 2

The compounds described herein were synthesized according to the following general Scheme 2

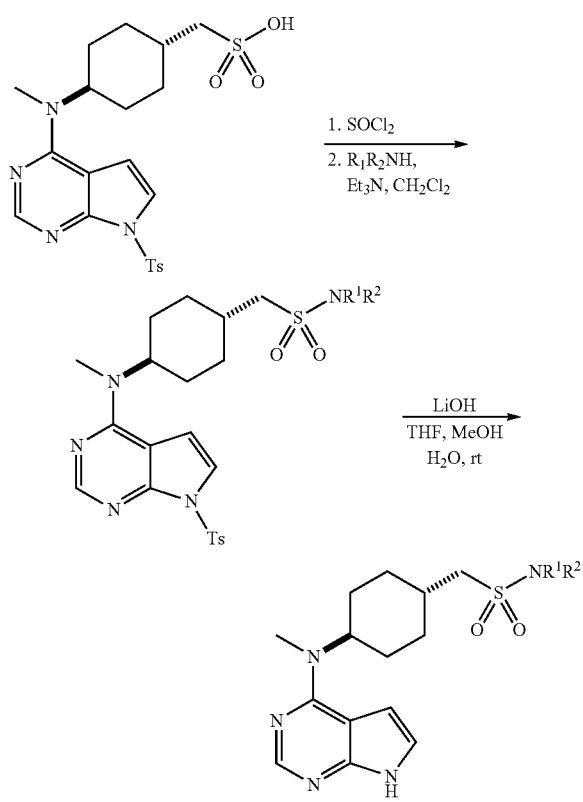

In the Examples, Ts refers to a tosyl group, having the following structure where ⌇⌇⌇ indicates the point of attachment:

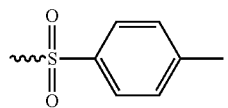

Step 1: To a 250 ml round bottom flask charged with ((1r,4r)-4-(methyl(7-tosyl-7H-pyrrolo[2,3-d]pyrimidin-4-yl)amino)cyclohexyl)methanesulfonic acid (4.2 g, 8.75 mmol), dichloromethane (80 mL) and N,N'-dimethylformamide (300 μL), thionyl chloride (10 mL) was added slowly over 10 minutes at 22-28° C. (the reaction was exothermic and gas evolved during addition). The reaction mixture was heated to reflux for 3 hours. The reaction was cooled to room temperature and stirred overnight under $N_2$. Most of solvents were evaporated at reduced pressure and then at high vacuum for at least 2 hours to give a dry brown solid which was used immediately for the next step without any purification.

Step 2: 2 mL (125 μmol) of freshly prepared sulfonyl chloride from Step 1 (0.0625M) in anhydrous N,N'-dimethylformamide was added to vial charged with 200 μmol of the appropriate amine, $R_1R_2NH$, followed by 100 μL of triethylamine. After the reaction mixture was shaken at room temperature for 16 hours, the solvent was evaporated under reduced pressure. A solution of 2 mL of 5% $Na_2CO_3$ and 2 mL of ethyl acetate were added to the vial. The mixture was vortexed and centrifuged. The organic phase was collected and concentrated to dryness under reduced pressure.

Step 3: Samples were re-dissolved in 1 mL of MeOH/THF/H2O (2/2/1, v/v/v). 0.1 mL of 2N lithium hydroxide (200 μmol) was added and the reaction mixtures were stirred at room temperature overnight. Solvent was removed and the samples were diluted with 1.5 mL of dimethylsulfoxide, purified by HPLC.

Example 1

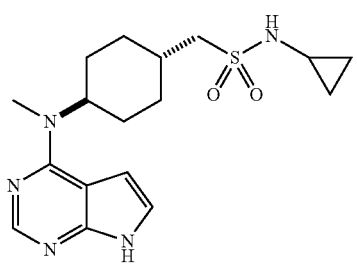

N-cyclopropyl-1-{trans-4-[methyl(7H-pyrrolo[2,3-d]pyrimidin-4-yl)amino]cyclohexyl}methanesulfonamide Step 1: Synthesis of N-cyclopropyl-1-{trans-4-[methyl(7H-pyrrolo[2,3-d]pyrimidin-4-yl)amino]cyclohexyl}methanesulfonamide Trans-4-(Methyl (7-tosyl-7H-pyrrolo[2,3-d]pyrimidin-4-yl)amino)cyclohexyl)methane-sulfonic acid (0.5 g, 1.04 mmol) was suspended in a solution of dichloromethane (4 mL) and N,N'-dimethylformamide (50 μL). The system was flushed with nitrogen and thionyl chloride (0.38 mL, 5.22 mmol) was added dropwise. The reaction mixture was heated at 40-45° C. for 2 hours, concentrated in vacuo and the residue was dissolved in chloroform (5 mL). Triethylamine (0.3 mL) was added followed by a solution of (3R)-3-pyrrolidinol (60 mg, 1.0 mmol) in chloroform (5 mL). The reaction mixture was stirred under nitrogen at room temperature overnight. The reaction mixture was diluted with ethyl acetate and washed with saturated aqueous $NaHCO_3$. The organic layer was washed with brine and concentrated in vacuo. The residue was dissolved in a mixture of tetrahydrofuran (3 mL), methanol (3 mL) and water (1 mL). Lithium hydroxide (50 mg, 2.08 mmol) was added and the reaction mixture was stirred at room temperature overnight. The reaction mixture was evaporated and water was added. The resulting precipitate was filtered and washed with water. The product was isolated as a white solid (201 mg, 53%). LCMS m/z 364.2 (M+H calcd for $C_{17}H_{25}N_5O_2S$ is 363.4). LCMS (C-18 column, gradient elution 10 minute chromatograph, 95:5 to 5:95 water/acetonitrile, retention time 3.38 min).

The compounds in Table 1 were synthesized according to General Synthetic Procedure 1

TABLE 1

| Example | Structure | Compound Name | Low Resolution LCMS (M + H) |
|---|---|---|---|
| 2 | 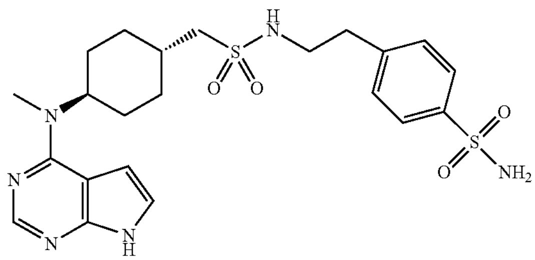 [SMILES: CN(c1ncnc2[nH]ccc12)[C@H]1CC[C@H](CS(=O)(=O)NCCc2ccc(S(N)(=O)=O)cc2)CC1] | 4-(2-{[({trans-4-[methyl(7H-pyrrolo[2,3-d]pyrimidin-4-yl)amino]cyclohexyl}methyl)sulfonyl]amino}ethyl)benzenesulfonamide | 507.1 |
| 3 | 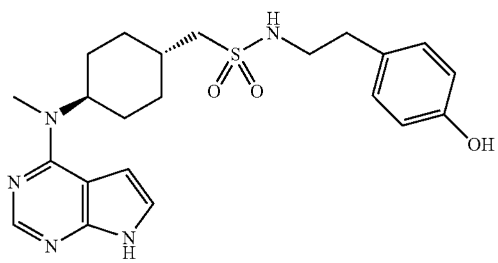 [SMILES: CN(c1ncnc2[nH]ccc12)[C@H]1CC[C@H](CS(=O)(=O)NCCc2ccc(O)cc2)CC1] | N-[2-(4-hydroxyphenyl)-ethyl]-1-{trans-4-[methyl-(7H-pyrrolo[2,3-d]pyrimidin-4-yl)amino]cyclohexyl}-methanesulfonamide | 444 |
| 4 | 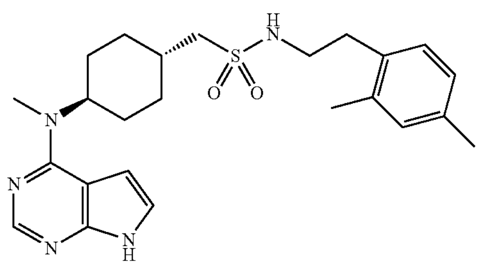 | N-[2-(2,4-dimethylphenyl)-ethyl]-1-{trans-4-[methyl-(7H-pyrrolo[2,3-d]pyrimidin-4-yl)amino]cyclohexyl}-methanesulfonamide | 456 |
| 5 | 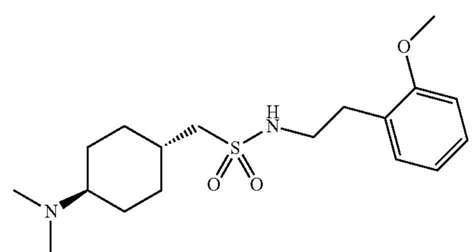 | N-[2-(2-methoxyphenyl)-ethyl]-1-{trans-4-[methyl-(7H-pyrrolo[2,3-d]pyrimidin-4-yl)amino]cyclohexyl}-methanesulfonamide | 458 |
| 6 | 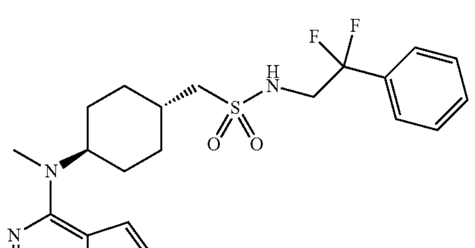 | N-(2,2-difluoro-2-phenyl-ethyl)-1-{trans-4-[methyl-(7H-pyrrolo[2,3-d]pyrimidin-4-yl)amino]cyclohexyl}-methanesulfonamide | 464 |

TABLE 1-continued

| Example | Structure | Compound Name | Low Resolution LCMS (M + H) |
|---|---|---|---|
| 7 | 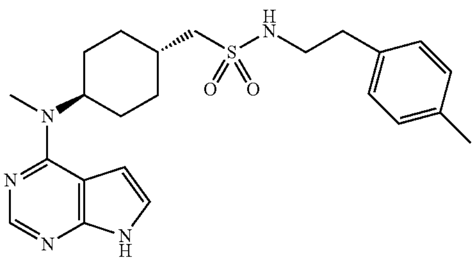 | N-[2-(4-methylphenyl)-ethyl]-1-{trans-4-[methyl-(7H-pyrrolo[2,3-d]pyrimidin-4-yl)amino]cyclohexyl}-methanesulfonamide | 442 |
| 8 | 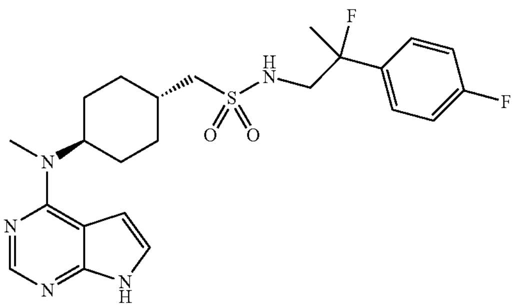 [SMILES: CN(c1ncnc2[nH]ccc12)[C@H]1CC[C@H](CS(=O)(=O)NCC(C)(F)c2ccc(F)cc2)CC1] | N-[2-fluoro-2-(4-fluorophenyl)propyl]-1-{trans-4-[methyl(7H-pyrrolo[2,3-d]-pyrimidin-4-yl)amino]-cyclohexyl}-methanesulfonamide | 478 |
| 9 | 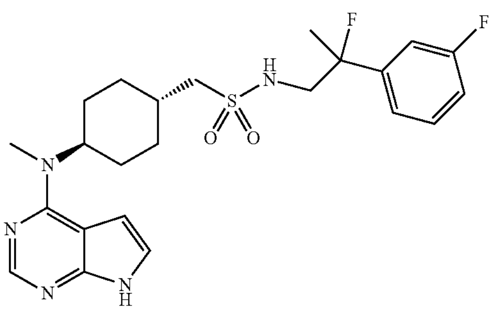 [SMILES: CN(c1ncnc2[nH]ccc12)[C@H]1CC[C@H](CS(=O)(=O)NCC(C)(F)c2cccc(F)c2)CC1] | N-[2-fluoro-2-(3-fluorophenyl)propyl]-1-{trans-4-[methyl(7H-pyrrolo[2,3-d]-pyrimidin-4-yl)amino]-cyclohexyl}-methanesulfonamide | 478 |
| 10 | 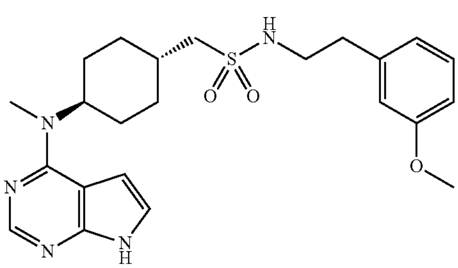 | N-[2-(3-methoxyphenyl)-ethyl]-1-{trans-4-[methyl-(7H-pyrrolo[2,3-d]pyrimidin-4-yl)amino]cyclohexyl}-methanesulfonamide | 458.2 |
| 11 | 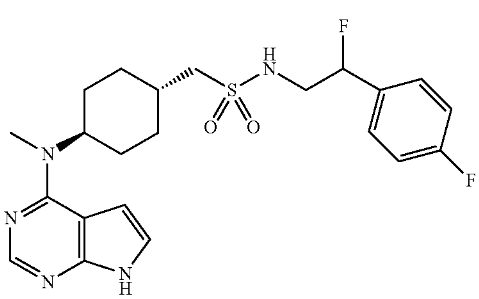 [SMILES: CN(c1ncnc2[nH]ccc12)[C@H]1CC[C@H](CS(=O)(=O)NCC(F)c2ccc(F)cc2)CC1] | N-[2-fluoro-2-(4-fluorophenyl)ethyl]-1-{trans-4-[methyl(7H-pyrrolo[2,3-d]-pyrimidin-4-yl)amino]-cyclohexyl}-methanesulfonamide | 464 |

TABLE 1-continued

| Example | Structure | Compound Name | Low Resolution LCMS (M + H) |
|---|---|---|---|
| 12 | 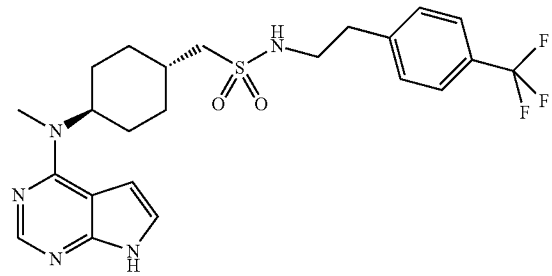 [SMILES: CN(c1ncnc2[nH]ccc12)[C@H]1CC[C@H](CS(=O)(=O)NCCc2ccc(C(F)(F)F)cc2)CC1] | 1-{trans-4-[methyl(7H-pyrrolo[2,3-d]pyrimidin-4-yl)amino]cyclohexyl}-N-{2-[4-(trifluoromethyl)-phenyl]ethyl}-methanesulfonamide | 496 |
| 13 | 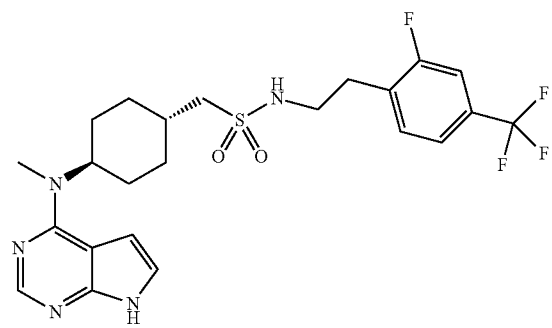 [SMILES: CN(c1ncnc2[nH]ccc12)[C@H]1CC[C@H](CS(=O)(=O)NCCc2ccc(C(F)(F)F)cc2F)CC1] | N-{2-[2-fluoro-4-(trifluoromethyl)phenyl]ethyl}-1-{trans-4-[methyl(7H-pyrrolo[2,3-d]pyrimidin-4-yl)amino]cyclohexyl}-methanesulfonamide | 514 |

Example 14

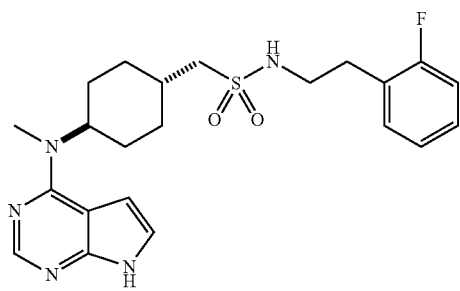

N-[2-(2-fluorophenyl)ethyl]-1-{trans-4-[methyl(7H-pyrrolo[2,3-d]pyrimidin-4-yl)amino] cyclohexyl}methanesulfonamide Step 1: To a 250 ml round bottom flask charged with ((1r,4r)-4-(methyl(7-tosyl-7H-pyrrolo[2,3-d]pyrimidin-4-yl)amino)cyclohexyl)methanesulfonic acid (4.2 g, 8.75 mmol), dichloromethane (80 mL) and N,N'-dimethylformamide (300 μL), thionyl chloride (10 mL) was added slowly over 10 minutes at 22-28° C. (the reaction was exothermic and gas evolved during addition). The reaction mixture was heated to reflux for 3 hours. The reaction was cooled to room temperature and stirred overnight under $N_2$. Most of solvents were evaporated at reduced pressure and then at high vacuum for at least 2 hours to give a dry brown solid which was used immediately for the next step without any purification.

Step 2: 2 mL (125 μmol) of freshly prepared sulfonyl chloride from Step 1 (0.0625M) in anhydrous N,N'-dimethylformamide was added to vial charged with 200 μmol of (2-fluorophenyl)ethyl amine, followed by 100 μL of triethylamine. After the reaction mixture was shaken at room temperature for 16 hours, the solvent was evaporated under reduced pressure. A solution of 2 mL of 5% $Na_2CO_3$ and 2 mL of ethyl acetate was added to the vial. The mixture was vortexed and centrifuged. The organic phase was collected and concentrated to dryness under reduced pressure. The sample were re-dissolved in 1 mL of MeOH/THF/H2O (2/2/1, v/v/v). 0.1 mL of 2N lithium hydroxide (200 μmol) was added and the reaction mixture was stirred at room temperature overnight. Solvent was removed and the sample was diluted with 1.5 mL of dimethylsulfoxide and purified by HPLC. LCMS m/z 446.3 (M+H calcd for $C_{22}H_{28}FN_5O_2S$ is 446.5).

The compounds in Table 2 were synthesized according to General Synthetic Procedure 2.

TABLE 2

| Example | Structure | Compound Name | Low Resolution LCMS (M + H) |
|---|---|---|---|
| 15 | 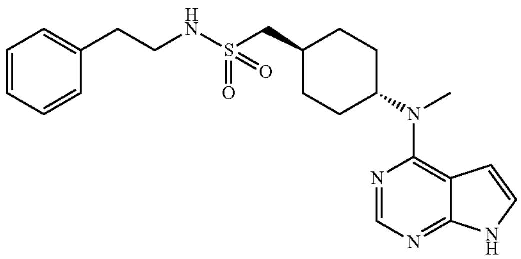 [SMILES: CN(c1ncnc2[nH]ccc12)[C@H]1CC[C@H](CS(=O)(=O)NCCc2ccccc2)CC1] | 1-{trans-4-[methyl(7H-pyrrolo-[2,3-d]pyrimidin-4-yl)amino]-cyclohexyl}-N-(2-phenylethyl)-methanesulfonamide | 428.1 |
| 16 | 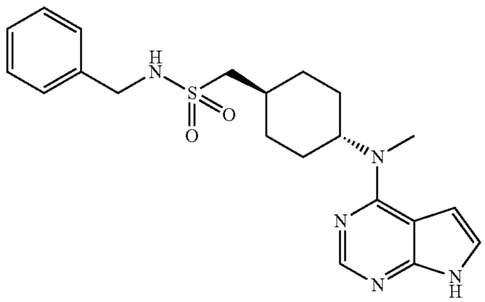 [SMILES: CN(c1ncnc2[nH]ccc12)[C@H]1CC[C@H](CS(=O)(=O)NCc2ccccc2)CC1] | N-benzyl-1-{trans-4-[methyl-(7H-pyrrolo[2,3-d]pyrimidin-4-yl)amino]-cyclohexyl}-methanesulfonamide | 414.6 |
| 17 | 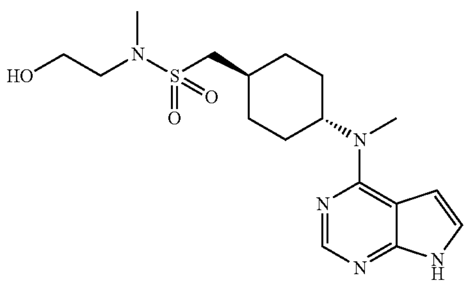 [SMILES: CN(CCO)S(=O)(=O)C[C@H]1CC[C@H](N(C)c2ncnc3[nH]ccc23)CC1] | N-(2-hydroxyethyl)-N-methyl-1-{trans-4-[methyl-(7H-pyrrolo[2,3-d]pyrimidin-4-yl)amino]cyclohexyl}-methanesulfonamide | 382.3 |
| 18 | 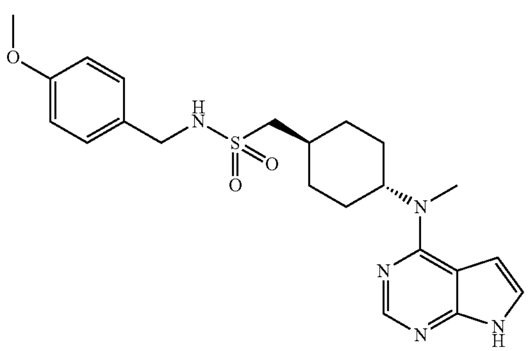 [SMILES: COc1ccc(CNS(=O)(=O)C[C@H]2CC[C@H](N(C)c3ncnc4[nH]ccc34)CC2)cc1] | N-(4-methoxybenzyl)-1-{trans-4-[methyl(7H-pyrrolo[2,3-d]-pyrimidin-4-yl)amino]-cyclo-hexyl}methanesulfonamide | 444.5 |
| 19 | 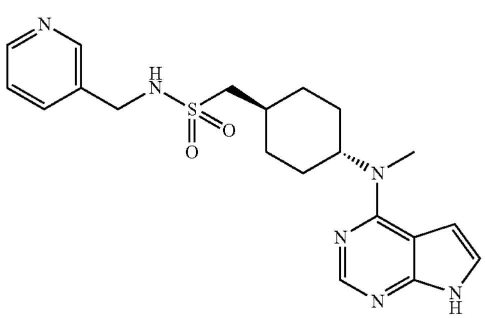 [SMILES: CN(c1ncnc2[nH]ccc12)[C@H]1CC[C@H](CS(=O)(=O)NCc2cccnc2)CC1] | 1-{trans-4-[methyl(7H-pyrrolo[2,3-d]pyrimidin-4-yl)amino]cyclohexyl}-N-(pyridin-3-ylmethyl)-methanesulfonamide | 415.5 |

TABLE 2-continued

| Example | Structure | Compound Name | Low Resolution LCMS (M + H) |
|---|---|---|---|
| 20 | 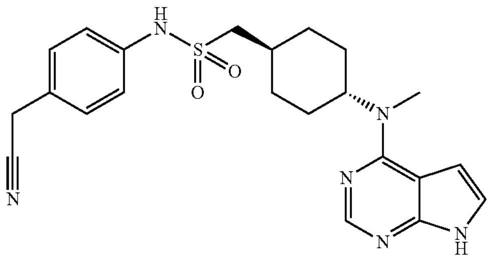 [SMILES: CN(c1ncnc2[nH]ccc12)[C@H]1CC[C@H](CS(=O)(=O)Nc2ccc(CC#N)cc2)CC1] | N-[4-(cyanomethyl)phenyl]-1-{trans-4-[methyl(7H-pyrrolo[2,3-d]pyrimidin-4-yl)amino]cyclohexyl}methane-sulfonamide | 439.1 |
| 21 | 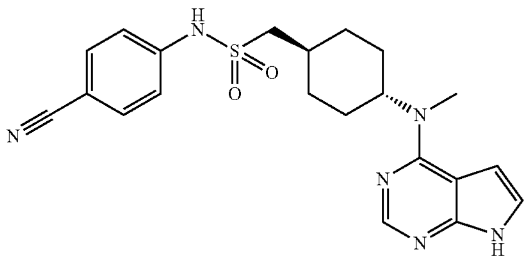 [SMILES: CN(c1ncnc2[nH]ccc12)[C@H]1CC[C@H](CS(=O)(=O)Nc2ccc(C#N)cc2)CC1] | N-(4-cyanophenyl)-1-{trans-4-[methyl(7H-pyrrolo[2,3-d]pyrimidin-4-yl)amino]cyclohexyl}-methanesulfonamide | 425.4 |
| 22 | 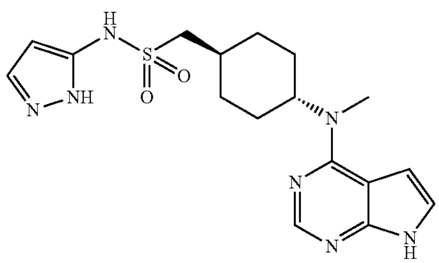 [SMILES: CN(c1ncnc2[nH]ccc12)[C@H]1CC[C@H](CS(=O)(=O)Nc2ccn[nH]2)CC1] | 1-{trans-4-[methyl(7H-pyrrolo[2,3-d]pyrimidin-4-yl)amino]cyclohexyl}-N-1H-pyrazol-5-yl-methanesulfonamide | 390.5 |
| 23 | 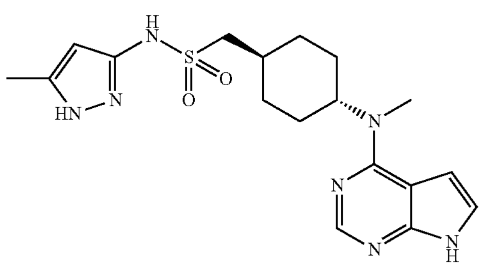 [SMILES: Cc1cc(NS(=O)(=O)C[C@H]2CC[C@H](N(C)c3ncnc4[nH]ccc34)CC2)n[nH]1] | N-(5-methyl-1H-pyrazol-3-yl)-1-{trans-4-[methyl(7H-pyrrolo[2,3-d]pyrimidin-4-yl)amino]cyclohexyl}-methanesulfonamide | 404.5 |
| 24 | 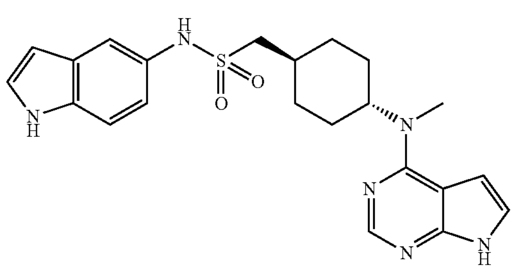 [SMILES: CN(c1ncnc2[nH]ccc12)[C@H]1CC[C@H](CS(=O)(=O)Nc2ccc3[nH]ccc3c2)CC1] | N-1H-indol-5-yl-1-{trans-4-[methyl(7H-pyrrolo[2,3-d]-pyrimidin-4-yl)amino]-cyclohexyl}-methanesulfonamide | 439.4 |

TABLE 2-continued

| Example | Structure | Compound Name | Low Resolution LCMS (M + H) |
|---|---|---|---|
| 25 | 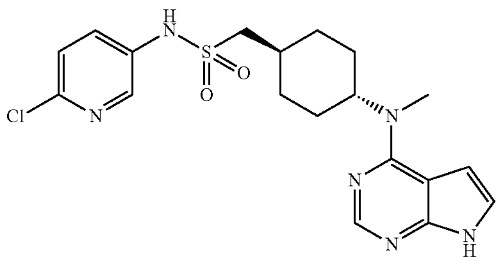 [SMILES: CN(c1ncnc2[nH]ccc12)[C@H]1CC[C@H](CS(=O)(=O)Nc2ccc(Cl)nc2)CC1] | N-(6-chloropyridin-3-yl)-1-{trans-4-[methyl(7H-pyrrolo[2,3-d]pyrimidin-4-yl)-amino]cyclohexyl}-methanesulfonamide | 435.1 |
| 26 | 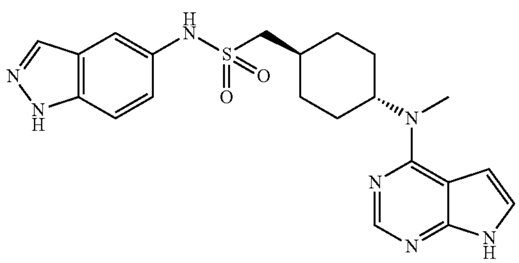 [SMILES: CN(c1ncnc2[nH]ccc12)[C@H]1CC[C@H](CS(=O)(=O)Nc2ccc3[nH]ncc3c2)CC1] | N-1H-indazol-5-yl-1-{trans-4-[methyl(7H-pyrrolo[2,3-d]pyrimidin-4-yl)amino]-cyclohexyl}-methanesulfonamide | 440.1 |
| 27 | 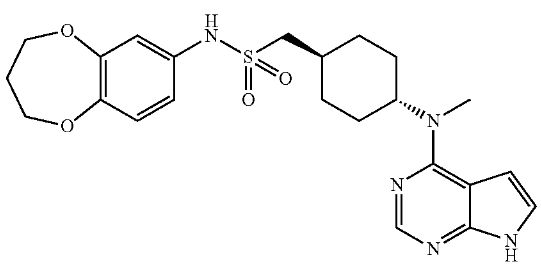 [SMILES: CN(c1ncnc2[nH]ccc12)[C@H]1CC[C@H](CS(=O)(=O)Nc2ccc3c(c2)OCCCO3)CC1] | N-(3,4-dihydro-2H-1,5-benzodioxepin-7-yl)-1-{trans-4-[methyl(7H-pyrrolo[2,3-d]pyrimidin-4-yl)amino]-cyclohexyl}methanesulfonamide | 472.4 |
| 28 | 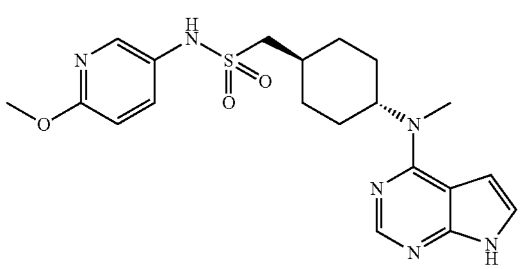 [SMILES: COc1ccc(NS(=O)(=O)C[C@H]2CC[C@H](N(C)c3ncnc4[nH]ccc34)CC2)cn1] | N-(6-methoxypyridin-3-yl)-1-{trans-4-[methyl(7H-pyrrolo[2,3-d]pyrimidin-4-yl)amino]cyclohexyl}methane-sulfonamide | 431.5 |
| 29 | 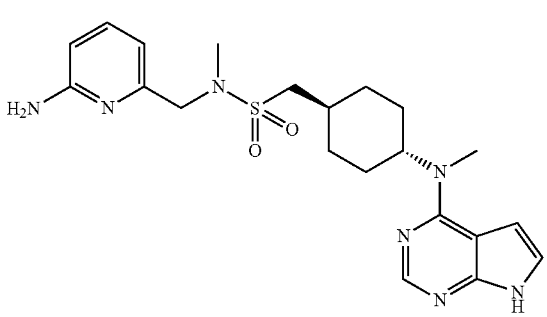 [SMILES: CN(Cc1cccc(N)n1)S(=O)(=O)C[C@H]1CC[C@H](N(C)c2ncnc3[nH]ccc23)CC1] | N-[(6-aminopyridin-2-yl)methyl]-N-methyl-1-{trans-4-[methyl(7H-pyrrolo[2,3-d]pyrimidin-4-yl)amino]cyclohexyl}-methanesulfonamide | 444.5 |

TABLE 2-continued

| Example | Structure | Compound Name | Low Resolution LCMS (M + H) |
|---|---|---|---|
| 30 | 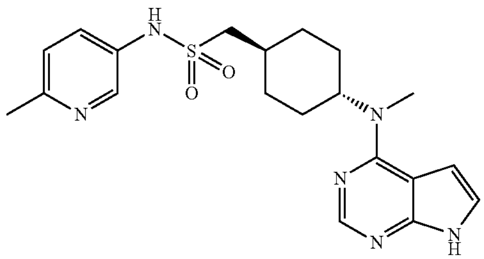 [SMILES: Cc1ccc(NS(=O)(=O)C[C@H]2CC[C@H](N(C)c3ncnc4[nH]ccc34)CC2)cn1] | N-(6-methylpyridin-3-yl)-1-{trans-4-[methyl(7H-pyrrolo[2,3-d]pyrimidin-4-yl)amino]cyclohexyl}-methanesulfonamide | 415.4 |
| 31 | 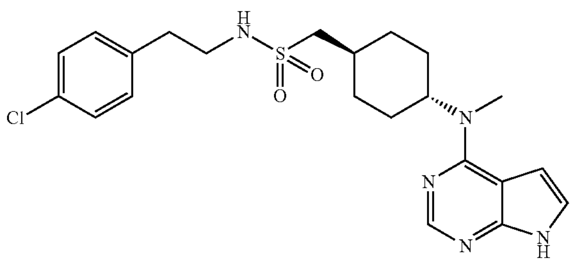 [SMILES: CN(c1ncnc2[nH]ccc12)[C@H]1CC[C@H](CS(=O)(=O)NCCc2ccc(Cl)cc2)CC1] | N-[2-(4-chlorophenyl)ethyl]-1-{trans-4-[methyl(7H-pyrrolo[2,3-d]pyrimidin-4-yl)amino]cyclohexyl}-methanesulfonamide | 462.35 |
| 32 | 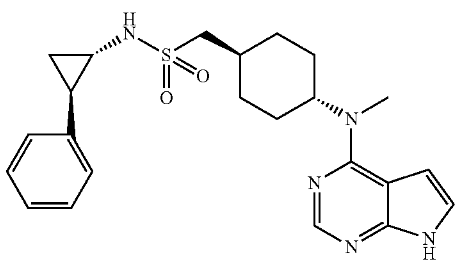 [SMILES: CN(c1ncnc2[nH]ccc12)[C@H]1CC[C@H](CS(=O)(=O)N[C@H]2C[C@@H]2c2ccccc2)CC1] | 1-{trans-4-[methyl(7H-pyrrolo[2,3-d]pyrimidin-4-yl)amino]cyclohexyl}-N-[(1S,2R)-2-phenylcyclopropyl]-methanesulfonamide | 440.35 |
| 33 | 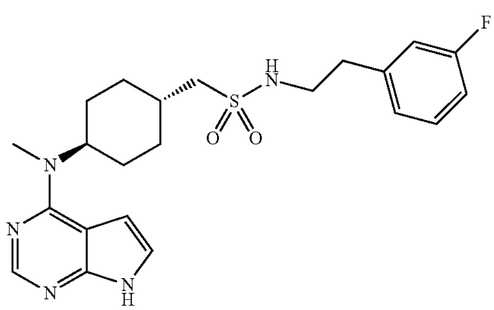 [SMILES: CN(c1ncnc2[nH]ccc12)[C@H]1CC[C@H](CS(=O)(=O)NCCc2cccc(F)c2)CC1] | N-[2-(3-fluorophenyl)ethyl]-1-{trans-4-[methyl(7H-pyrrolo[2,3-d]pyrimidin-4-yl)amino]cyclohexyl}-methanesulfonamide | 446.35 |
| 34 | 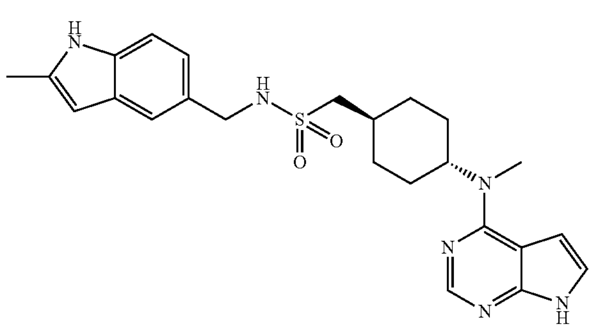 [SMILES: Cc1cc2cc(CNS(=O)(=O)C[C@H]3CC[C@H](N(C)c4ncnc5[nH]ccc45)CC3)ccc2[nH]1] | N-[(2-methyl-1H-indol-5-yl)methyl]-1-{trans-4-[methyl(7H-pyrrolo[2,3-d]-pyrimidin-4-yl)amino]-cyclohexyl}-methanesulfonamide | 467.15 |

TABLE 2-continued

| Example | Structure | Compound Name | Low Resolution LCMS (M + H) |
|---|---|---|---|
| 35 | 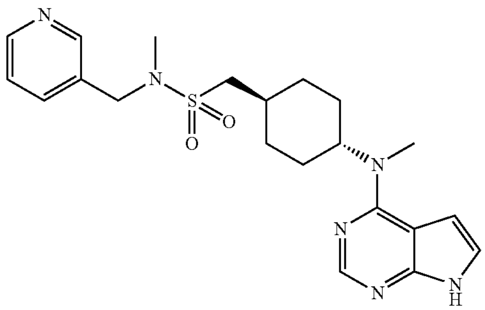 [SMILES: CN(Cc1cccnc1)S(=O)(=O)C[C@H]1CC[C@H](N(C)c2ncnc3[nH]ccc23)CC1] | N-methyl-1-{trans-4-[methyl(7H-pyrrolo[2,3-d]-pyrimidin-4-yl)amino]-cyclohexyl}-N-(pyridin-3-ylmethyl)-methanesulfonamide | 429.35 |
| 36 | 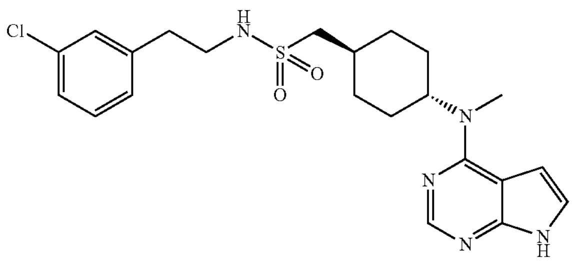 [SMILES: CN(c1ncnc2[nH]ccc12)[C@H]1CC[C@H](CS(=O)(=O)NCCc2cccc(Cl)c2)CC1] | N-[2-(3-chlorophenyl)ethyl]-1-{trans-4-[methyl(7H-pyrrolo[2,3-d]pyrimidin-4-yl)amino]cyclohexyl}-methanesulfonamide | 462.35 |
| 37 | 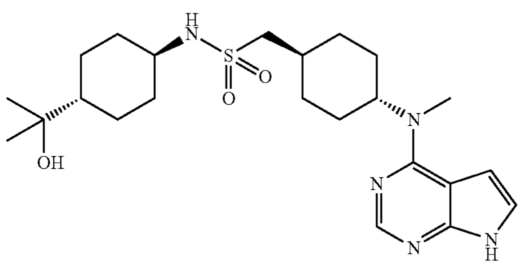 [SMILES: CN(c1ncnc2[nH]ccc12)[C@H]1CC[C@H](CS(=O)(=O)N[C@H]2CC[C@H](C(C)(C)O)CC2)CC1] | N-[trans-4-(1-hydroxy-1-methylethyl)cyclohexyl]-1-{trans-4-[methyl(7H-pyrrolo[2,3-d]pyrimidin-4-yl)amino]cyclohexyl}-methanesulfonamide | 464.25 |
| 38 | 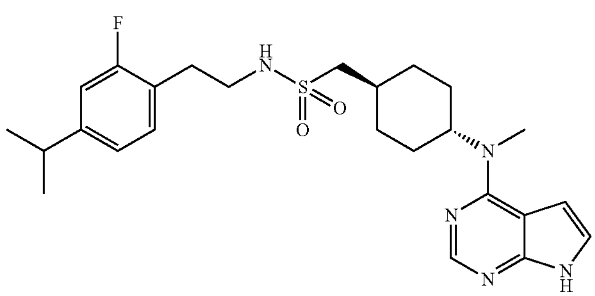 [SMILES: CC(C)c1ccc(CCNS(=O)(=O)C[C@H]2CC[C@H](N(C)c3ncnc4[nH]ccc34)CC2)c(F)c1] | N-[2-(2-fluoro-4-isopropylphenyl)ethyl]-1-{trans-4-[methyl(7H-pyrrolo[2,3-d]pyrimidin-4-yl)amino]cyclohexyl}-methanesulfonamide | 488.25 |
| 39 | 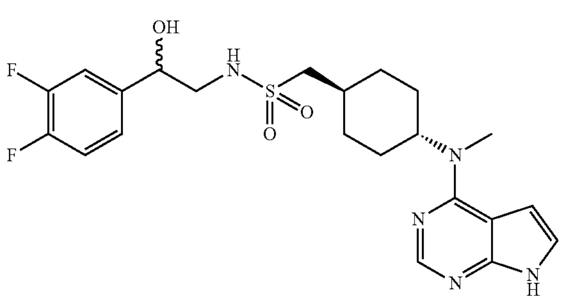 [SMILES: CN(c1ncnc2[nH]ccc12)[C@H]1CC[C@H](CS(=O)(=O)NCC(O)c2ccc(F)c(F)c2)CC1] | N-[2-(3,4-difluorophenyl)-2-hydroxyethyl]-1-{trans-4-[methyl(7H-pyrrolo[2,3-d]pyrimidin-4-yl)amino]-cyclohexyl}-methanesulfonamide | 480.25 |

TABLE 2-continued

| Example | Structure | Compound Name | Low Resolution LCMS (M + H) |
|---|---|---|---|
| 40 | 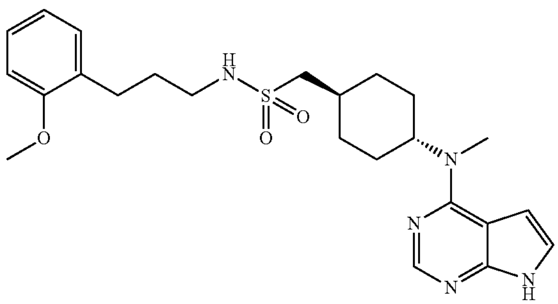 [SMILES: COc1ccccc1CCCNS(=O)(=O)C[C@H]1CC[C@H](N(C)c2ncnc3[nH]ccc23)CC1] | N-[3-(2-methoxyphenyl)-propyl]-1-{trans-4-[methyl(7H-pyrrolo[2,3-d]-pyrimidin-4-yl)amino]-cyclohexyl}-methanesulfonamide | 472.35 |
| 41 | 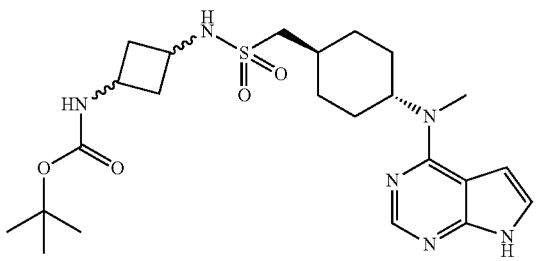 [SMILES: CN(c1ncnc2[nH]ccc12)[C@H]1CC[C@H](CS(=O)(=O)NC2CC(NC(=O)OC(C)(C)C)C2)CC1] | tert-butyl (3-{[({trans-4-[methyl(7H-pyrrolo[2,3-d]-pyrimidin-4-yl)amino]-cyclohexyl}methyl)sulfonyl]amino}cyclobutyl)-carbamate | 493.35 |
| 42 | 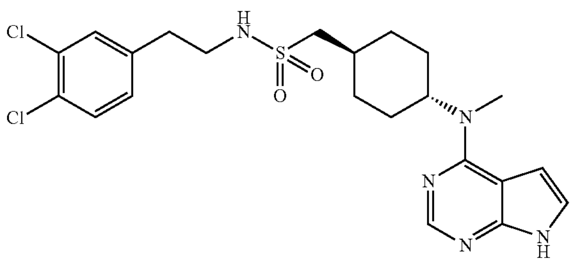 [SMILES: CN(c1ncnc2[nH]ccc12)[C@H]1CC[C@H](CS(=O)(=O)NCCc2ccc(Cl)c(Cl)c2)CC1] | N-[2-(3,4-dichlorophenyl)-ethyl]-1-{trans-4-[methyl-(7H-pyrrolo[2,3-d]pyrimidin-4-yl)amino]cyclohexyl}-methanesulfonamide | 496.55 |
| 43 | 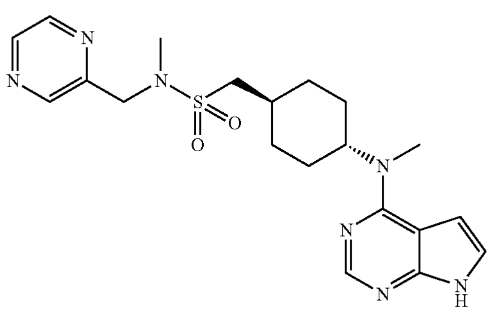 [SMILES: CN(Cc1cnccn1)S(=O)(=O)C[C@H]1CC[C@H](N(C)c2ncnc3[nH]ccc23)CC1] | N-methyl-1-{trans-4-[methyl(7H-pyrrolo[2,3-d]-pyrimidin-4-yl)amino]-cyclohexyl}-N-(pyrazin-2-ylmethyl)-methanesulfonamide | 430.45 |
| 44 | 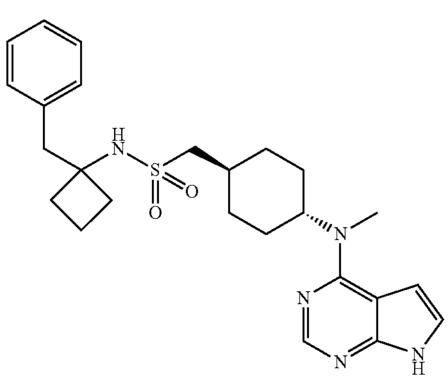 [SMILES: CN(c1ncnc2[nH]ccc12)[C@H]1CC[C@H](CS(=O)(=O)NC2(Cc3ccccc3)CCC2)CC1] | N-(1-benzylcyclobutyl)-1-{trans-4-[methyl(7H-pyrrolo-[2,3-d]pyrimidin-4-yl)amino]-cyclohexyl}methane-sulfonamide | 468.65 |

TABLE 2-continued

| Example | Structure | Compound Name | Low Resolution LCMS (M + H) |
|---|---|---|---|
| 45 | 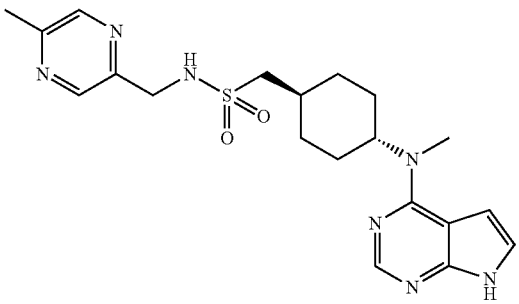 [SMILES: Cc1cnc(CNS(=O)(=O)C[C@H]2CC[C@H](N(C)c3ncnc4[nH]ccc34)CC2)cn1] | N-[(5-methylpyrazin-2-yl)methyl]-1-{trans-4-[methyl(7H-pyrrolo[2,3-d]-pyrimidin-4-yl)amino]cyclohexyl}-methanesulfonamide | 430.35 |
| 46 | 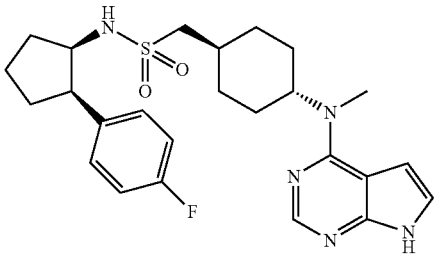 [SMILES: CN(c1ncnc2[nH]ccc12)[C@H]1CC[C@H](CS(=O)(=O)N[C@@H]2CCC[C@@H]2c2ccc(F)cc2)CC1] | N-[(1R,2R)-2-(4-fluoro-phenyl)cyclopentyl]-1-{trans-4-[methyl(7H-pyrrolo[2,3-d]pyrimidin-4-yl)amino]cyclohexyl}-methanesulfonamide | 486.55 |
| 47 | 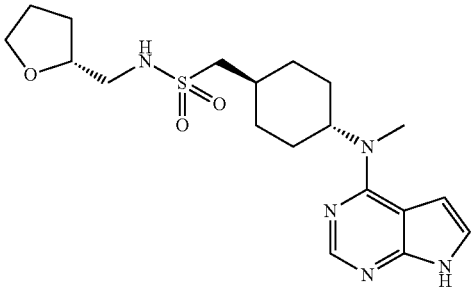 [SMILES: CN(c1ncnc2[nH]ccc12)[C@H]1CC[C@H](CS(=O)(=O)NC[C@H]2CCCO2)CC1] | 1-{trans-4-[methyl(7H-pyrrolo[2,3-d]pyrimidin-4-yl)amino]cyclohexyl}-N-[(2R)-tetrahydrofuran-2-ylmethyl]-methanesulfonamide | 408.35 |
| 48 | 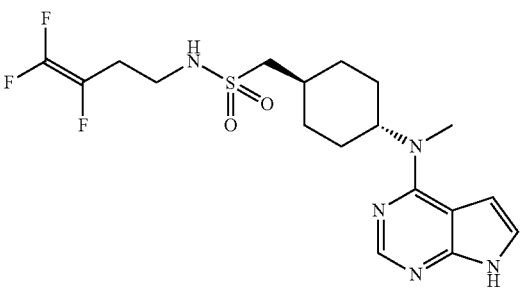 [SMILES: CN(c1ncnc2[nH]ccc12)[C@H]1CC[C@H](CS(=O)(=O)NCCC(F)=C(F)F)CC1] | 1-{trans-4-[methyl(7H-pyrrolo[2,3-d]pyrimidin-4-yl)amino]cyclohexyl}-N-(3,4,4-trifluorobut-3-en-1-yl)methanesulfonamide | 432.35 |
| 49 | 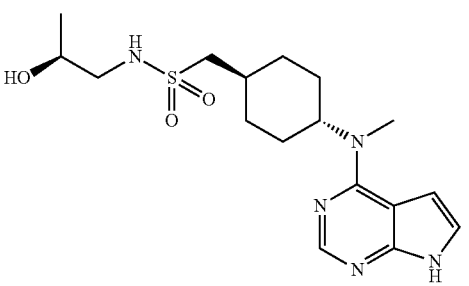 [SMILES: C[C@H](O)CNS(=O)(=O)C[C@H]1CC[C@H](N(C)c2ncnc3[nH]ccc23)CC1] | N-[(2S)-2-hydroxypropyl]-1-{trans-4-[methyl(7H-pyrrolo[2,3-d]pyrimidin-4-yl)amino]cyclohexyl}-methanesulfonamide | 382.15 |

TABLE 2-continued

| Example | Structure | Compound Name | Low Resolution LCMS (M + H) |
|---|---|---|---|
| 50 | 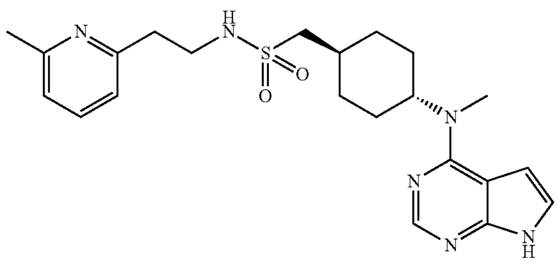 [SMILES: Cc1cccc(CCNS(=O)(=O)C[C@H]2CC[C@H](N(C)c3ncnc4[nH]ccc34)CC2)n1] | N-[2-(6-methylpyridin-2-yl)ethyl]-1-{trans-4-[methyl(7H-pyrrolo[2,3-d]-pyrimidin-4-yl)amino]-cyclohexyl}-methanesulfonamide | 443.45 |
| 51 | 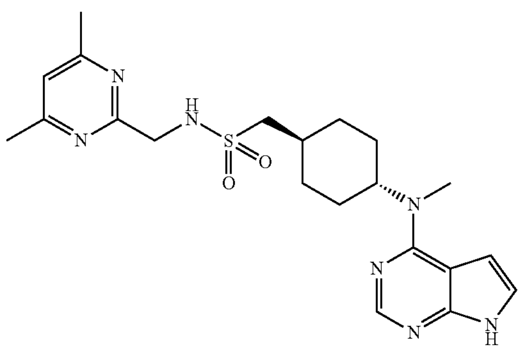 [SMILES: Cc1cc(C)nc(CNS(=O)(=O)C[C@H]2CC[C@H](N(C)c3ncnc4[nH]ccc34)CC2)n1] | N-[(4,6-dimethylpyrimidin-2-yl)methyl]-1-{trans-4-[methyl(7H-pyrrolo[2,3-d]-pyrimidin-4-yl)amino]cyclohexyl}-methanesulfonamide | 444.45 |
| 52 | 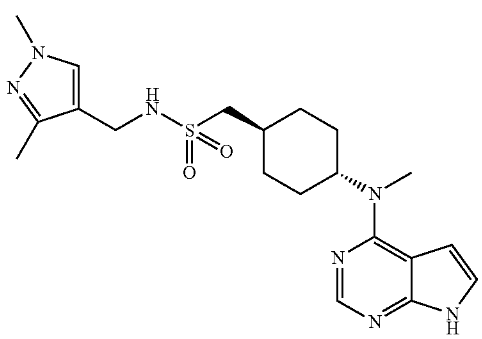 [SMILES: Cc1nn(C)cc1CNS(=O)(=O)C[C@H]1CC[C@H](N(C)c2ncnc3[nH]ccc23)CC1] | N-[(1,3-dimethyl-1H-pyrazol-4-yl)methyl]-1-{trans-4-[methyl(7H-pyrrolo[2,3-d]pyrimidin-4-yl)amino]cyclohexyl}-methanesulfonamide | 432.35 |
| 53 | 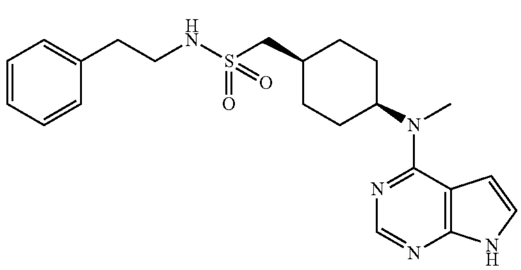 [SMILES: CN(c1ncnc2[nH]ccc12)[C@H]1CC[C@@H](CS(=O)(=O)NCCc2ccccc2)CC1] | 1-{cis-4-[methyl(7H-pyrrolo[2,3-d]pyrimidin-4-yl)amino]cyclohexyl}-N-(2-phenylethyl)-methanesulfonamide | 428.0 |
| 54 | 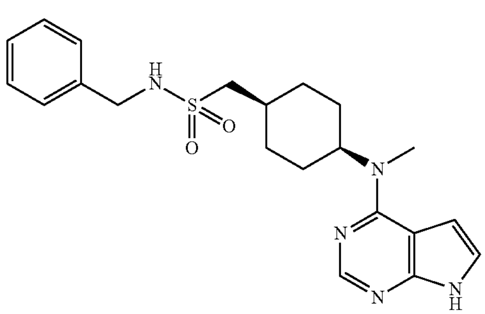 [SMILES: CN(c1ncnc2[nH]ccc12)[C@H]1CC[C@@H](CS(=O)(=O)NCc2ccccc2)CC1] | N-benzyl-1-{cis-4-[methyl(7H-pyrrolo[2,3-d]pyrimidin-4-yl)amino]cyclohexyl}-methanesulfonamide | 414.5 |

TABLE 2-continued

| Example | Structure | Compound Name | Low Resolution LCMS (M + H) |
|---|---|---|---|
| 55 | 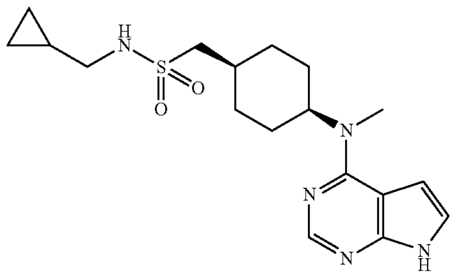 [SMILES: CN(c1ncnc2[nH]ccc12)[C@H]1CC[C@@H](CS(=O)(=O)NCC2CC2)CC1] | N-(cyclopropylmethyl)-1-{cis-4-[methyl(7H-pyrrolo[2,3-d]pyrimidin-4-yl)amino]cyclohexyl}-methanesulfonamide | 378.1 |
| 56 | 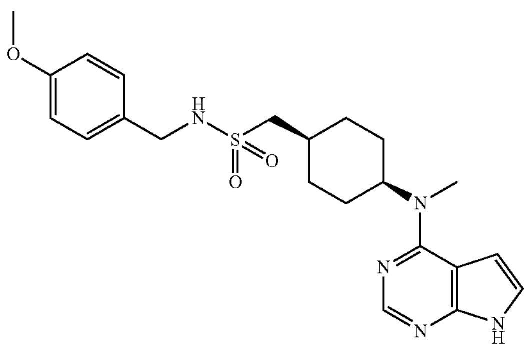 [SMILES: COc1ccc(CNS(=O)(=O)C[C@H]2CC[C@@H](N(C)c3ncnc4[nH]ccc34)CC2)cc1] | N-(4-methoxybenzyl)-1-{cis-4-[methyl(7H-pyrrolo[2,3-d]pyrimidin-4-yl)amino]cyclohexyl}-methanesulfonamide | 444.5 |

Example 57

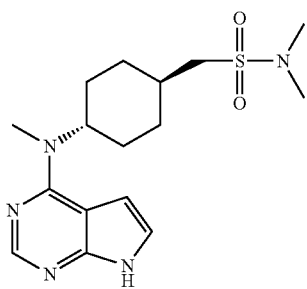 [SMILES: CN(C)S(=O)(=O)C[C@H]1CC[C@H](N(C)c2ncnc3[nH]ccc23)CC1]

N,N-dimethyl((1r,4r)-4-(methyl(7H-pyrrolo[2,3-d]pyrimidin-4-yl)amino)-cyclohexyl)-methanesulfonamide Step 1: To a chloroform (2 ml) solution of ((1r,4r)-4-(methyl(7-tosyl-7H-pyrrolo[2,3-d]-pyrimidin-4-yl)amino)cyclohexyl)methanesulfonyl chloride (100 mg, 0.20 mmols) was added a solution of 2.0M dimethylamine in THF (1.0 ml,). The reaction was stirred at room temperature for one hour. The volatiles were removed by rotary evaporation at low pressure to afford a viscous oil. The oil was dissolved in a small volume of methylene chloride and applied to a 10 g cartridge of silica gel. The cartridge was eluted with an acetone/heptane gradient which provided pure product, N,N-dimethyl((1r,4r)-4-(methyl(7-tosyl-7H pyrrolo[2,3-d]pyrimidin-4-yl)amino)cyclohexyl)methanesulfonamide, as a white solid (76 mg, 75%).

Step 2: To a methanolic (5 ml) mixture of N,N-dimethyl ((1r,4r)-4-(methyl(7-tosyl-7H pyrrolo[2,3-d]pyrimidin-4-yl) amino)cyclohexyl)methanesulfonamide was added cesium carbonate (97 mg, 0.3 mmols). The reaction was stirred at 50 degrees Celcius for four hours. The product was precipitated in pure form through the addition of water (10 ml) to the reaction mixture. The product, N,N-dimethyl((1r,4r)-4-(methyl(7H-pyrrolo[2,3-d]pyrimidin-4-yl)amino)cyclohexyl) methanesulfonamide was captured by suction filtration and dried under vacuum (36 mg, 66%) $^1$H NMR (400 MHz, CHLOROFORM-d) d ppm 1.35-1.47 (m, 2H) 1.68-1.79 (m, 2H) 1.88-1.97 (m, 2H) 2.02-2.10 (m, 1H) 2.17-2.25 (m, 2H) 2.83 (d, J=6.32 Hz, 2H) 2.91 (s, 6H) 3.26 (s, 3H) 4.82 (br. s., 1H) 6.57 (d, J=3.28 Hz, 1H) 7.05 (d, J=2.78 Hz, 1H) 8.32 (s, 1H) 9.98 (br. s., 1H); m/z (CI) 352 ([M+H]$^+$.

Biological Evaluation
JAK Enzymatic Assay
Materials

Recombinant JAK1 (Catalog Number PV4775), JAK2 (Catalog Number PV4210) and JAK3 (Catalog Number PV3855) were purchased from (Invitrogen Corporation, Madison, Wis.). Tyk2 (His-Tyk2 (888-1182, C936S, C1142S)) used in this study was expressed and purified at Pfizer Laboratories. Adenosine 5'-triphosphate (ATP) was obtained from (Sigma Chemical Company, St. Louis, Mo.).

The JAKtide peptide (peptide sequence, FITC-KGGEEEEY-FELVKK) used for the JAK2 and JAK3 assays and the IRS-1 peptide (peptide sequence, 5-FAM-KKSRGDYMTMQIG) used for the JAK1 and Tyk2 assays were purchased from (American Peptide Company, Sunnyvale, Calif.). Coating Reagent 3 was purchased from (Caliper Life Sciences, Hopkinton, Mass.).

Methods

A peptide mobility shift assay was used to quantify the phosphorylation of the JAKtide (JAK2 and JAK3) or the IRS-1 peptide (JAM and Tyk2). Reactions were carried out in a 384-well plate (Matrical MP-101) in a 10 µL total volume. Reaction mixtures contained 20 mM HEPES, pH 7.4, 10 mM magnesium chloride, 0.01% bovine serum albumin (BSA), 0.0005% Tween-20, ATP (4 µM for JAK2 and JAK3, 40 µM for JAK1 and 7 µM for Tyk2)), 2% DMSO and 1 µM peptide substrate (JAKtide for JAK2 and JAK3 and IRS-1 peptide for JAK1 and Tyk2). Compounds were diluted serially in 100% dimethyl sulfoxide and tested in an 11 point dose response in duplicate or quadruplicate (200 nl of compound/DMSO was added per 10 µL reaction). The reactions were initiated by the addition of enzyme to the final concentration of 2 nM JAK2, 1 nM JAK3, 12 nM Tyk2 or 20 nM JAK1. The assay was run for 240 minutes for JAK1, 150 minutes for JAK2, 90 minutes for JAK3 and 70 minutes for Tyk2. The assays were stopped at the specified times with 20 uL of 140 mM HEPES, 22.5 mM EDTA and 0.15% Coating Reagent 3. The plates were placed on a LabChip 3000 (LC3000) instrument from (Caliper Life Sciences) to measure the formation of phosphorylated peptide. Data was analyzed using Hits Well Analyzer Software from (Caliper Life Sciences) to obtain the amount of product formed.

Data was then imported into an internal application where each data point is expressed as % inhibition based on uninhibited and no enzyme controls. Dose-response data is then fit using a 4 parameter logistic equation (Equation 1) to determine an $IC_{50}$.

Equation 1:

$$y = \frac{max - min}{1 + \left(\frac{x}{IC_{50}}\right)^s} + min$$

Where max is the fitted uninhibited value, min is the fitted complete inhibition value, and s is the slope factor.

Using this protocol, the following results were generated:

| Example | JAK3:IC50 (µM) | JAK2:IC50 (µM) | JAK1:IC50 (µM) |
|---|---|---|---|
| 1 | 0.224 | 0.0454 | 0.01 |
| 2 | 0.166 | 0.0149 | 0.00182 |
| 3 | 0.257 | 0.0286 | 0.00225 |
| 4 | 0.139 | 0.00917 | 0.00301 |
| 5 | 0.188 | 0.017 | 0.00378 |
| 6 | 0.101 | 0.0118 | 0.00422 |
| 7 | 0.137 | 0.0113 | 0.00444 |
| 8 | 0.403 | 0.0323 | 0.00605 |
| 9 | 0.531 | 0.0397 | 0.0105 |
| 10 | 0.301 | 0.0341 | 0.011 |
| 11 | 0.424 | 0.0619 | 0.0135 |
| 12 | 0.511 | 0.0555 | 0.0165 |
| 13 | 0.563 | 0.0553 | 0.0174 |
| 14 | 0.148 | 0.0205 | 0.00465 |
| 15 | 0.0878 | 0.012 | 0.00287 |
| 16 | 0.182 | 0.0294 | 0.0135 |
| 17 | 0.332 | 0.0442 | 0.0163 |
| 18 | 0.175 | 0.0275 | 0.0213 |
| 19 | 0.376 | 0.0579 | 0.0093 |
| 20 | 0.0961 | 0.0381 | 0.00958 |
| 21 | 0.14 | 0.0524 | 0.0103 |
| 22 | 0.241 | 0.0324 | 0.0152 |
| 23 | 0.342 | 0.0305 | 0.0186 |
| 24 | 0.0558 | 0.00455 | 0.00165 |
| 25 | 0.228 | 0.0574 | 0.0186 |
| 26 | 0.175 | 0.0394 | 0.019 |
| 27 | 0.0543 | 0.00747 | 0.00219 |
| 28 | 0.121 | 0.0222 | 0.00872 |
| 29 | 0.514 | 0.051 | 0.0167 |
| 30 | 0.221 | 0.0476 | 0.0165 |
| 31 | 0.154 | 0.019 | 0.00367 |
| 32 | 0.144 | 0.0236 | 0.00434 |
| 33 | 0.192 | 0.0242 | 0.00495 |
| 34 | 0.224 | 0.0247 | 0.00676 |
| 35 | 0.622 | 0.0761 | 0.00685 |
| 36 | 0.294 | 0.0414 | 0.0077 |
| 37 | 0.212 | 0.0333 | 0.00873 |
| 38 | 0.145 | 0.0554 | 0.00913 |
| 39 | 0.24 | 0.0306 | 0.00979 |
| 40 | 0.208 | 0.0298 | 0.0107 |
| 41 | 0.292 | 0.123 | 0.0116 |
| 42 | 0.427 | 0.0557 | 0.0145 |
| 43 | 0.517 | 0.0532 | 0.0149 |
| 44 | 0.641 | 0.112 | 0.0151 |
| 45 | 0.49 | 0.0497 | 0.0153 |
| 46 | 0.355 | 0.0184 | 0.0156 |
| 47 | 1.06 | 0.174 | 0.0161 |
| 48 | 0.267 | 0.066 | 0.0196 |
| 49 | 0.526 | 0.0642 | 0.0214 |
| 50 | 0.633 | 0.0806 | 0.0216 |
| 51 | 0.237 | 0.0202 | 0.0233 |
| 52 | 0.762 | 0.107 | 0.024 |
| 53 | 0.119 | 0.0347 | 0.0115 |
| 54 | 0.162 | 0.0542 | 0.0193 |
| 55 | 0.201 | 0.0341 | 0.0114 |
| 56 | 0.114 | 0.0366 | 0.0107 |
| 57 | 0.174 | 0.0275 | 0.00733 |

Mouse Collagen Induced Arthritis Model

Male DBA/1 mice, 8-10 weeks of age (18-22 g), are obtained from Harlan Laboratories (Indianapolis, Ind.) and provided food and water ad libitum. Mice are immunized subcutaneously with 50 µg of chicken type II collagen (Dr. Marie Griffiths, University of Utah) emulsified in complete Freund's adjuvant (Sigma, St. Louis, Mo.), and boosted 21 days later with 50 µg of the same antigen in incomplete Freund's adjuvant (Sigma). The compound is resuspended in 0.5% methylcellulose/0.025% Tween-20 (Sigma) containing 50 mM citric acid monohydrate, pH 3 (Fisher Scientific; Pittsburgh, Pa.). Mice are administered vehicle or varying doses of the compound by oral gavage, and disease is monitored daily beginning on day 35 post-immunization. Severity is scored on a scale of 0-3 in each paw (maximum score of 12/mouse), where 0=no symptoms, 1=redness or swelling of digits of the paw, 2=gross swelling or deformity of the whole paw, 3=ankylosis of the joint, and is expressed as the average severity score for each treatment group. Area under the curve (AUC) from a time course of disease severity is calculated for each dose of compound and percent of control activity is used as a measure of efficacy.

As used herein, reference to "a" or "an" means "one or more." Throughout, the plural and singular should be treated as interchangeable, other than the indication of number.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. For example, the range $C_1$-$C_6$, includes the subranges $C_2$-$C_6$, $C_3$-$C_6$, $C_3$-$C_5$, $C_4$-$C_6$, etc., as well as $C_1$ (methyl), $C_2$ (ethyl), $C_3$ (propyl), $C_4$ (butyl), $C_5$ (pentyl) and $C_6$ (hexyl) individually. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as, in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion of one or more of any of the group members in the claimed invention.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

The above detailed description of embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:
1. A compound of Formula I:

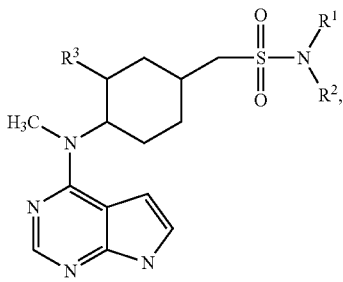

Formula I or a pharmaceutically acceptable salt thereof; wherein:
$R^1$ is selected from the group consisting of hydrogen and $(C_1-C_6)$alkyl; and
when $R^1$ is hydrogen, then $R^2$ is selected from the group consisting of $(C_5-C_6)$alkyl, halo$(C_1-C_6)$alkyl, $(C_3-C_6)$cycloalkyl$(C_1-C_6)$alkyl, hydroxy$(C_5-C_6)$alkyl, $(C_1-C_6)$alkenyl, halo$(C_1-C_6)$alkenyl, phenyl, phenyl$(C_1-C_6)$alkyl, $(C_3-C_6)$cycloalkyl, heterocyclyl, and heterocyclyl $(C_1-C_6)$alkyl;
when $R^1$ is $(C_1-C_6)$alkyl, then $R^2$ is selected from the group consisting of $(C_1-C_6)$alkyl, halo$(C_1-C_6)$alkyl, $(C_3-C_6)$cycloalkyl$(C_1-C_6)$alkyl, hydroxy$(C_1-C_6)$alkyl, $(C_1-C_6)$alkenyl, phenyl, phenyl$(C_1-C_6)$alkyl, $(C_3-C_6)$cycloalkyl, heterocyclyl, and heterocyclyl$(C_1-C_6)$alkyl;
wherein $(C_3-C_6)$cycloalkyl, wherever it occurs, is optionally substituted with one or more substituents selected from the group consisting of hydroxy$(C_1-C_6)$alkyl, phenyl, phenyl$(C_1-C_6)$alkyl, and $(C_1-C_6)$alkoxycarbonylamino; and
wherein when $R^1$ is hydrogen and $R^2$ is cyclobutyl, then the cyclobutyl is substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino;
wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, aminosulfonyl, and $(C_1-C_6)$alkylaminosulfonyl;
wherein heterocyclyl, wherever it occurs, is optionally substituted with one or more substituents independently selected from the group consisting of halo, $(C_1-C_6)$alkyl, $(C_1-C_6)$alkoxy, amino, and $(C_1-C_6)$alkylamino; and
wherein the $(C_1-C_6)$alkyl in phenyl$(C_1-C_6)$alkyl and heterocyclyl$(C_1-C_6)$alkyl is optionally substituted with one more substituents independently selected from the group consisting of halo and hydroxy; and
$R^3$ selected from the group consisting of hydrogen and $(C_1-C_6)$alkyl.

2. The compound of claim 1, wherein
$R^1$ is selected from the group consisting of hydrogen and $(C_1-C_6)$alkyl; and
when $R^1$ is hydrogen, then $R^2$ is selected from the group consisting of $(C_5-C_6)$alkyl, halo$(C_1-C_6)$alkyl, $(C_3-C_6)$cycloalkyl$(C_1-C_6)$alkyl, hydroxy$(C_5-C_6)$alkyl, halo$(C_1-C_6)$alkenyl, phenyl, phenyl$(C_1-C_6)$alkyl, cyclopropyl, cyclobutyl, cyclopentyl, cyclohexyl, indolyl, indazolyl, pyridinyl, pyrazolyl, 3,4-dihydro-2H-benzo[b][1,4]dioxepinyl, indolylmethyl, pyridinylmethyl, pyrimidinylmethyl, pyrazinylmethyl, pyrazolylmethyl, tetrahydrofuranylmethyl, and pyridinylethyl; and
when $R^1$ is $(C_1-C_6)$alkyl, then $R^2$ is selected from the group consisting of $(C_1-C_6)$alkyl, halo$(C_1-C_6)$alkyl, hydroxy$(C_1-C_6)$alkyl, phenyl, phenyl$(C_1-C_6)$alkyl, pyrazinylmethyl, and pyridinylmethyl;
wherein cyclopropyl, cyclobutyl, cyclopentyl, and cyclohexyl, wherever they occur, are optionally substituted with one or more substituents selected from the group consisting of hydroxy$(C_1-C_6)$alkyl, phenyl, phenyl$(C_1-C_6)$alkyl, and $(C_1-C_6)$alkoxycarbonylamino; and wherein when $R^1$ is hydrogen and $R^2$ is cyclobutyl, then the cyclobutyl is substituted with one or more substituents selected from the group consisting of hydroxy$(C_1-C_6)$alkyl, phenyl, phenyl$(C_1-C_6)$alkyl, and $(C_1-C_6)$alkoxycarbonylamino;
wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, and aminosulfonyl;
wherein indolyl, indazolyl, pyridinyl, pyrimidinyl, pyrazinyl, pyrazolyl, 3,4-dihydro-2H-benzo[b][1,4]dioxepinyl, and tetrahydrofuranyl, wherever they occur, are optionally substituted with one or more substituents independently selected from the group consisting of halo, $(C_1-C_6)$alkyl, $(C_1-C_6)$alkoxy, and amino; and
wherein the $(C_1-C_6)$alkyl in phenyl$(C_1-C_6)$alkyl is optionally substituted with one more substituents independently selected from the group consisting of halo and hydroxy; and
$R^3$ selected from the group consisting of hydrogen and $(C_1-C_6)$alkyl.

3. The compound of claim 1, wherein
$R^1$ is hydrogen;
$R^2$ is selected from the group consisting of $(C_5-C_6)$alkyl, halo$(C_1-C_6)$alkyl, $(C_3-C_6)$cycloalkyl$(C_1-C_6)$alkyl, hydroxy$(C_5-C_6)$alkyl, $(C_1-C_6)$alkenyl, and halo$(C_1-C_6)$alkenyl;
wherein the $(C_3-C_6)$cycloalkyl in $(C_3-C_6)$cycloalkyl$(C_1-C_6)$alkyl is optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and
$R^3$ selected from the group consisting of hydrogen and $(C_1-C_6)$alkyl.

4. The compound of claim 3, wherein
$R^1$ is hydrogen;
$R^2$ is selected from the group consisting of $(C_5-C_6)$alkyl, halo$(C_1-C_6)$alkyl, $(C_3-C_6)$cycloalkyl$(C_1-C_6)$alkyl, hydroxy$(C_5-C_6)$alkyl, $(C_1-C_6)$alkenyl, and halo$(C_1-C_6)$alkenyl; wherein the $(C_3-C_6)$cycloalkyl in $(C_3-C_6)$cycloalkyl$(C_1-C_6)$alkyl is optionally substituted with one or more substituents selected from the group consisting of hydroxy$(C_1-C_6)$alkyl, phenyl, halophenyl, phenyl $(C_1-C_6)$alkyl, and $(C_1-C_6)$alkoxycarbonylamino; and
$R^3$ selected from the group consisting of hydrogen and methyl.

5. The compound of claim 4, wherein
$R^1$ is hydrogen;
$R^2$ is selected from the group consisting of cyclopropylmethyl and trifluorobutenyl; and
$R^3$ selected from the group consisting of hydrogen and methyl.

6. The compound of claim 1, wherein
$R^1$ is $(C_1-C_6)$alkyl;
$R^2$ is selected from the group consisting of $(C_1-C_6)$alkyl, halo$(C_1-C_6)$alkyl, $(C_3-C_6)$cycloalkyl$(C_1-C_6)$alkyl, hydroxy$(C_1-C_6)$alkyl, $(C_1-C_6)$alkenyl, and halo$(C_1-C_6)$alkenyl;
wherein the $(C_3-C_6)$cycloalkyl in $(C_3-C_6)$cycloalkyl$(C_1-C_6)$alkyl is optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and
$R^3$ selected from the group consisting of hydrogen and $(C_1-C_6)$alkyl.

7. The compound of claim 6, wherein
$R^1$ is $(C_1-C_6)$alkyl;
$R^2$ is selected from the group consisting of $(C_1-C_6)$alkyl, halo$(C_1-C_6)$alkyl, $(C_3-C_6)$cycloalkyl$(C_1-C_6)$alkyl, and hydroxy$(C_1-C_6)$alkyl;
wherein the $(C_3-C_6)$cycloalkyl in $(C_3-C_6)$cycloalkyl$(C_1-C_6)$alkyl is optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and
$R^3$ selected from the group consisting of hydrogen and methyl.

8. The compound of claim 6, wherein
$R^1$ is $(C_1-C_6)$alkyl;
$R^2$ is selected from the group consisting of $(C_1-C_6)$alkyl and hydroxy$(C_1-C_6)$alkyl; and
$R^3$ selected from the group consisting of hydrogen and $(C_1-C_6)$alkyl.

9. The compound of claim 6, wherein
$R^1$ is methyl;
$R^2$ is selected from the group consisting of methyl and hydroxyethyl; and
$R^3$ selected from the group consisting of hydrogen and methyl.

10. The compound of claim 1, wherein
$R^1$ is selected from the group consisting of hydrogen and $(C_1-C_6)$alkyl; and
$R^2$ is selected from the group consisting of cyclopropyl, cyclobutyl, cyclopentyl, and cyclohexyl;
wherein cyclopropyl, cyclobutyl, cyclopentyl, and cyclohexyl are optionally substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and
wherein when $R^1$ is hydrogen and $R^2$ is cyclobutyl, then the cyclobutyl is substituted with one or more substituents selected from the group consisting of hydroxy$(C_1-C_6)$alkyl, phenyl, halophenyl, phenyl$(C_1-C_6)$alkyl, and $(C_1-C_6)$alkoxycarbonylamino; and
$R^3$ selected from the group consisting of hydrogen and $(C_1-C_6)$alkyl.

11. The compound of claim 10, wherein
$R^1$ is selected from the group consisting of hydrogen and $(C_1-C_6)$alkyl; and
$R^2$ is selected from the group consisting of cyclopropyl, cyclobutyl, cyclopentyl, and cyclohexyl;
wherein cyclopropyl, cyclobutyl, cyclopentyl, and cyclohexyl are optionally substituted with one or more substituents selected from the group consisting of hydroxypropyl, phenyl, fluorophenyl, phenylmethyl and tert-butoxycarbonylamino; and
wherein when $R^1$ is hydrogen and $R^2$ is cyclobutyl, then the cyclobutyl is substituted with one or more substituents selected from the group consisting of hydroxypropyl, phenyl, fluorophenyl, phenylmethyl and tert-butoxycarbonylamino; and
$R^3$ selected from the group consisting of hydrogen and $(C_1-C_6)$alkyl.

12. The compound of claim 11, wherein $R^1$ is hydrogen.

13. The compound of claim 11, wherein $R^1$ is $(C_1-C_6)$alkyl.

14. The compound of claim 11, wherein
$R^1$ is selected from the group consisting of hydrogen and methyl; and
$R^2$ is selected from the group consisting of cyclopropyl, cyclobutyl, cyclopentyl, and cyclohexyl;
wherein cyclopropyl, cyclobutyl, cyclopentyl, and cyclohexyl are optionally substituted with one or more substituents selected from the group consisting of hydroxypropyl, phenyl, fluorophenyl, phenylmethyl and tert-butoxycarbonylamino; and
wherein when $R^1$ is hydrogen and $R^2$ is cyclobutyl, then the cyclobutyl is substituted with one or more substituents selected from the group consisting of hydroxypropyl, phenyl, fluorophenyl, phenylmethyl and tert-butoxycarbonylamino; and
$R^3$ selected from the group consisting of hydrogen and methyl.

15. The compound of claim 11, wherein
$R^1$ is hydrogen;
$R^2$ is selected from the group consisting of cyclopropyl, fluorophenylcyclopentyl, hydroxypropylcyclohexyl, and tert-butoxycarbonylaminocyclobutyl; and
$R^3$ selected from the group consisting of hydrogen and methyl.

16. The compound of claim 1, wherein
$R^1$ is selected from the group consisting of hydrogen and $(C_1-C_6)$alkyl;
$R^2$ is selected from the group consisting of phenyl, phenyl$(C_1-C_6)$alkyl, heterocyclyl, and heterocyclyl$(C_1-C_6)$alkyl; and
wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, and aminosulfonyl;
wherein heterocyclyl, wherever it occurs, is optionally substituted with one or more substituents independently selected from the group consisting of halo, $(C_1-C_6)$alkyl, $(C_1-C_6)$alkoxy, and amino; and
wherein the $(C_1-C_6)$alkyl in phenyl$(C_1-C_6)$alkyl and heterocyclyl$(C_1-C_6)$alkyl is optionally substituted with one more substituents independently selected from the group consisting of halo and hydroxy; and
$R^3$ selected from the group consisting of hydrogen and $(C_1-C_6)$alkyl.

17. The compound of claim 16, wherein
$R^1$ is selected from the group consisting of hydrogen and $(C_1-C_6)$alkyl;
$R^2$ is selected from the group consisting of phenyl and phenyl$(C_1-C_6)$alkyl; and
wherein phenyl, wherever it occurs, is optionally substituted with one or more substituents independently selected from the group consisting of cyano, halo, hydroxy, $(C_1-C_6)$alkyl, halo$(C_1-C_6)$alkyl, cyano$(C_1-C_6)$alkyl, $(C_1-C_6)$alkoxy, and aminosulfonyl; and
wherein the $(C_1-C_6)$alkyl in phenyl$(C_1-C_6)$alkyl is optionally substituted with one more substituents independently selected from the group consisting of halo and hydroxy; and

63

R³ selected from the group consisting of hydrogen and (C₁-C₆)alkyl.

18. The compound of claim 17, wherein
R¹ is selected from the group consisting of hydrogen and (C₁-C₆)alkyl;
R² is selected from the group consisting of phenyl and phenyl(C₁-C₄)alkyl;
wherein phenyl, wherever it occurs, is optionally substituted with one or more substituents independently selected from the group consisting of cyano, chloro, fluoro, hydroxy, methyl, trifluoromethyl, cyanomethyl, methoxy, and aminosulfonyl; and
wherein the (C₁-C₄)alkyl in phenyl(C₁-C₄)alkyl is optionally substituted with one more substituents independently selected from the group consisting of fluoro and hydroxy; and
R³ is selected from the group consisting of hydrogen and methyl.

19. The compound of claim 18, wherein
R¹ is selected from the group consisting of hydrogen and methyl;
R² is selected from the group consisting of phenyl and phenyl(C₁-C₄)alkyl;
wherein phenyl, wherever it occurs, is optionally substituted with one or more substituents independently selected from the group consisting of cyano, chloro, fluoro, hydroxy, methyl, trifluoromethyl, cyanomethyl, methoxy, and aminosulfonyl; and
wherein the (C₁-C₄)alkyl in phenyl(C₁-C₄)alkyl is optionally substituted with one more substituents independently selected from the group consisting of fluoro and hydroxy; and
R³ is selected from the group consisting of hydrogen and methyl.

20. The compound of claim 16, wherein
R¹ is selected from the group consisting of hydrogen and (C₁-C₆)alkyl;
R² is selected from the group consisting of heterocyclyl and heterocyclyl(C₁-C₆)alkyl; and
wherein heterocyclyl, wherever it occurs, is optionally substituted with one or more substituents independently selected from the group consisting of halo, (C₁-C₆)alkyl, (C₁-C₆)alkoxy, and amino; and
wherein the (C₁-C₆)alkyl in heterocyclyl(C₁-C₆)alkyl is optionally substituted with one more substituents independently selected from the group consisting of halo and hydroxy; and
R³ selected from the group consisting of hydrogen and (C₁-C₆)alkyl.

21. The compound of claim 20, wherein
R¹ is selected from the group consisting of hydrogen and (C₁-C₆)alkyl;
R² is selected from the group consisting of 3-12 membered ring heterocyclyl and 3-12 membered ring heterocyclyl (C₁-C₆)alkyl; and
wherein heterocyclyl, wherever it occurs, is optionally substituted with one or more substituents independently selected from the group consisting of halo, (C₁-C₆)alkyl, (C₁-C₆)alkoxy, and amino; and
wherein the (C₁-C₆)alkyl in heterocyclyl(C₁-C₆)alkyl is optionally substituted with one more substituents independently selected from the group consisting of halo and hydroxy; and
R³ selected from the group consisting of hydrogen and (C₁-C₆)alkyl.

64

22. The compound of claim 21, wherein
R¹ is selected from the group consisting of hydrogen and (C₁-C₆)alkyl;
R² is selected from the group consisting of indolyl, indazolyl, pyridinyl, pyrimidinyl, pyrazinyl, pyrazolyl, 3,4-dihydro-2H-benzo[b][1,4]dioxepinyl, tetrahydrofuranyl, indolyl(C₁-C₆)alkyl, indazolyl(C₁-C₆)alkyl, pyridinyl(C₁-C₆)alkyl, pyrimidinyl(C₁-C₆)alkyl, pyrazinyl(C₁-C₆)alkyl, pyrazolyl(C₁-C₆)alkyl, 3,4-dihydro-2H-benzo[b][1,4]dioxepinyl(C₁-C₆)alkyl, and tetrahydrofuranyl(C₁-C₆)alkyl; and
wherein indolyl, indazolyl, pyridinyl, pyrimidinyl, pyrazinyl, pyrazolyl, 3,4-dihydro-2H-benzo[b][1,4]dioxepinyl, tetrahydrofuranyl are optionally substituted with one or more substituents independently selected from the group consisting of halo, (C₁-C₆)alkyl, (C₁-C₆)alkoxy, and amino; and
wherein the (C₁-C₆)alkyl in indolyl(C₁-C₆)alkyl, indazolyl (C₁-C₆)alkyl, pyridinyl(C₁-C₆)alkyl, pyrimidinyl(C₁-C₆)alkyl, pyrazinyl(C₁-C₆)alkyl, pyrazolyl(C₁-C₆) alkyl, 3,4-dihydro-2H-benzo[b][1,4]dioxepinyl(C₁-C₆) alkyl, and tetrahydrofuranyl(C₁-C₆)alkyl is optionally substituted with one more substituents independently selected from the group consisting of halo and hydroxy; and
R³ selected from the group consisting of hydrogen and (C₁-C₆)alkyl.

23. The compound of claim 21, wherein
R¹ is selected from the group consisting of hydrogen and (C₁-C₆)alkyl;
R² is selected from the group consisting of indolyl, indazolyl, pyridinyl, pyrazolyl, 3,4-dihydro-2H-benzo[b][1,4]dioxepinyl, indolylmethyl, pyridinylmethyl, pyrimidinylmethyl, pyrazinylmethyl, pyrazolylmethyl, tetrahydrofuranylmethyl, and pyridinylethyl; and
wherein indolyl, indazolyl, pyridinyl, pyrimidinyl, pyrazinyl, pyrazolyl, 3,4-dihydro-2H-benzo[b][1,4]dioxepinyl, and tetrahydrofuranyl are optionally substituted with one or more substituents independently selected from the group consisting of halo, (C₁-C₆)alkyl, (C₁-C₆) alkoxy, and amino; and
R³ selected from the group consisting of hydrogen and (C₁-C₆)alkyl.

24. The compound of claim 23, wherein
R¹ is selected from the group consisting of hydrogen and methyl;
R² is selected from the group consisting of indolyl, indazolyl, pyridinyl, pyrazolyl, 3,4-dihydro-2H-benzo[b][1,4]dioxepinyl, indolylmethyl, pyridinylmethyl, pyrimidinylmethyl, pyrazinylmethyl, pyrazolylmethyl, tetrahydrofuranylmethyl, and pyridinylethyl;
wherein indolyl, indazolyl, pyridinyl, pyrimidinyl, pyrazinyl, pyrazolyl, 3,4-dihydro-2H-benzo[b][1,4]dioxepinyl, and tetrahydrofuranyl, are optionally substituted with one or more substituents independently selected from the group consisting of chloro, methyl, methoxy, and amino; and
R³ selected from the group consisting of hydrogen and methyl.

25. The compound of claim 1, wherein the compound is selected from the group consisting of:
N-(cyclopropylmethyl)-1-{cis-4-[methyl(7H-pyrrolo[2,3-d]pyrimidin-4-yl)amino]cyclohexyl}methanesulfonamide;
1-{trans-4-[methyl(7H-pyrrolo[2,3-d]pyrimidin-4-yl)amino]cyclohexyl}-N-(3,4,4-trifluorobut-3-en-1-yl)methanesulfonamide;

N-(2-hydroxyethyl)-N-methyl-1-{trans-4-[methyl(7H-pyrrolo[2,3-d]pyrimidin-4-yl)amino]cyclohexyl}methanesulfonamide;

N-[(6-aminopyridin-2-yl)methyl]-N-methyl-1-{trans-4-[methyl(7H-pyrrolo[2,3-d]pyrimidin-4-yl)amino]cyclohexyl}methanesulfonamide;

N-methyl-1-{trans-4-[methyl(7H-pyrrolo[2,3-d]pyrimidin-4-yl)amino]cyclohexyl}-N-(pyridin-3-ylmethyl)methanesulfonamide;

N-methyl-1-{trans-4-[methyl(7H-pyrrolo[2,3-d]pyrimidin-4-yl)amino]cyclohexyl}-N-(pyrazin-2-ylmethyl)methanesulfonamide;

N,N-dimethyl((1r,4r)-4-(methyl(7H-pyrrolo[2,3-d]pyrimidin-4-yl)amino)cyclohexyl)methanesulfonamide;

N-cyclopropyl-1-{trans-4-[methyl(7H-pyrrolo[2,3-d]pyrimidin-4-yl)amino]cyclohexyl}methanesulfonamide;

N-[trans-4-(1-hydroxy-1-methylethyl)cyclohexyl]-1-{trans-4-[methyl(7H-pyrrolo[2,3-d]pyrimidin-4-yl)amino]cyclohexyl}methanesulfonamide;

tert-butyl (3-{[({trans-4-[methyl(7H-pyrrolo[2,3-d]pyrimidin-4-yl)amino]cyclohexyl}methyl)sulfonyl]amino}cyclobutyl)carbamate;

N-[(1R,2R)-2-(4-fluorophenyl)cyclopentyl]-1-{trans-4-[methyl(7H-pyrrolo[2,3-d]pyrimidin-4-yl)amino]cyclohexyl}methanesulfonamide;

N-(1-benzylcyclobutyl)-1-{trans-4-[methyl(7H-pyrrolo[2,3-d]pyrimidin-4-yl)amino]cyclohexyl}methanesulfonamide;

1-{trans-4-[methyl(7H-pyrrolo[2,3-d]pyrimidin-4-yl)amino]cyclohexyl}-N-[(1S,2R)-2-phenylcyclopropyl]methanesulfonamide;

-(2-{[({trans-4-[methyl(7H-pyrrolo[2,3-d]pyrimidin-4-yl)amino]cyclohexyl}methyl)sulfonyl]amino}ethyl)benzenesulfonamide;

N-[2-(4-hydroxyphenyl)ethyl]-1-{trans-4-[methyl(7H-pyrrolo[2,3-d]pyrimidin-4-yl)amino]cyclohexyl}methanesulfonamide;

N-[2-(2,4-dimethylphenyl)ethyl]-1-{trans-4-[methyl(7H-pyrrolo[2,3-d]pyrimidin-4-yl)amino]cyclohexyl}methanesulfonamide;

N-[2-(2-methoxyphenyl)ethyl]-1-{trans-4-[methyl(7H-pyrrolo[2,3-d]pyrimidin-4-yl)amino]cyclohexyl}methanesulfonamide;

N-(2,2-difluoro-2-phenylethyl)-1-{trans-4-[methyl(7H-pyrrolo[2,3-d]pyrimidin-4-yl)amino]cyclohexyl}methanesulfonamide;

N-[2-(4-methylphenyl)ethyl]-1-{trans-4-[methyl(7H-pyrrolo[2,3-d]pyrimidin-4-yl)amino]cyclohexyl}methanesulfonamide;

N-[2-fluoro-2-(4-fluorophenyl)propyl]-1-{trans-4-[methyl(7H-pyrrolo[2,3-d]pyrimidin-4-yl)amino]cyclohexyl}methanesulfonamide;

N-[2-fluoro-2-(3-fluorophenyl)propyl]-1-{trans-4-[methyl(7H-pyrrolo[2,3-d]pyrimidin-4-yl)amino]cyclohexyl}methanesulfonamide;

N-[2-(3-methoxyphenyl)ethyl]-1-{trans-4-[methyl(7H-pyrrolo[2,3-d]pyrimidin-4-yl)amino]cyclohexyl}methanesulfonamide;

N-[2-fluoro-2-(4-fluorophenyl)ethyl]-1-{trans-4-[methyl(7H-pyrrolo[2,3-d]pyrimidin-4-yl)amino]cyclohexyl}methanesulfonamide;

1-{trans-4-[methyl(7H-pyrrolo[2,3-d]pyrimidin-4-yl)amino]cyclohexyl}-N-{2-[4-(trifluoromethyl)phenyl]ethyl}methanesulfonamide;

N-{2-[2-fluoro-4-(trifluoromethyl)phenyl]ethyl}-1-{trans-4-[methyl(7H-pyrrolo[2,3-d]pyrimidin-4-yl)amino]cyclohexyl}methanesulfonamide;

1-{trans-4-[methyl(7H-pyrrolo[2,3-d]pyrimidin-4-yl)amino]cyclohexyl}-N-(2-phenylethyl)methanesulfonamide;

N-benzyl-1-{trans-4-[methyl(7H-pyrrolo[2,3-d]pyrimidin-4-yl)amino]cyclohexyl}methanesulfonamide;

N-(4-methoxybenzyl)-1-{trans-4-[methyl(7H-pyrrolo[2,3-d]pyrimidin-4-yl)amino]cyclohexyl}methanesulfonamide;

N-[4-(cyanomethyl)phenyl]-1-{trans-4-[methyl(7H-pyrrolo[2,3-d]pyrimidin-4-yl)amino]cyclohexyl}methanesulfonamide;

N-(4-cyanophenyl)-1-{trans-4-[methyl(7H-pyrrolo[2,3-d]pyrimidin-4-yl)amino]cyclohexyl}methanesulfonamide;

N-[2-(4-chlorophenyl)ethyl]-1-{trans-4-[methyl(7H-pyrrolo[2,3-d]pyrimidin-4-yl)amino]cyclohexyl}methanesulfonamide;

N-[2-(2-fluorophenyl)ethyl]-1-{trans-4-[methyl(7H-pyrrolo[2,3-d]pyrimidin-4-yl)amino]cyclohexyl}methanesulfonamide;

N-[2-(3-fluorophenyl)ethyl]-1-{trans-4-[methyl(7H-pyrrolo[2,3-d]pyrimidin-4-yl)amino]cyclohexyl}methanesulfonamide;

N-[2-(3-chlorophenyl)ethyl]-1-{trans-4-[methyl(7H-pyrrolo[2,3-d]pyrimidin-4-yl)amino]cyclohexyl}methanesulfonamide;

N-[2-(2-fluoro-4-isopropylphenyl)ethyl]-1-{trans-4-[methyl(7H-pyrrolo[2,3-d]pyrimidin-4-yl)amino]cyclohexyl}methanesulfonamide;

N-[2-(3,4-difluorophenyl)-2-hydroxyethyl]-1-{trans-4-[methyl(7H-pyrrolo[2,3-d]pyrimidin-4-yl)amino]cyclohexyl}methanesulfonamide;

N-[3-(2-methoxyphenyl)propyl]-1-{trans-4-[methyl(7H-pyrrolo[2,3-d]pyrimidin-4-yl)amino]cyclohexyl}methanesulfonamide;

N-[2-(3,4-dichlorophenyl)ethyl]-1-{trans-4-[methyl(7H-pyrrolo[2,3-d]pyrimidin-4-yl)amino]cyclohexyl}methanesulfonamide;

1-{cis-4-[methyl(7H-pyrrolo[2,3-d]pyrimidin-4-yl)amino]cyclohexyl}-N-(2-phenylethyl)methanesulfonamide;

N-benzyl-1-{cis-4-[methyl(7H-pyrrolo[2,3-d]pyrimidin-4-yl)amino]cyclohexyl}methanesulfonamide;

N-(4-methoxybenzyl)-1-{cis-4-[methyl(7H-pyrrolo[2,3-d]pyrimidin-4-yl)amino]cyclohexyl}methanesulfonamide;

1-{trans-4-[methyl(7H-pyrrolo[2,3-d]pyrimidin-4-yl)amino]cyclohexyl}-N-(pyridin-3-ylmethyl)methanesulfonamide;

1-{trans-4-[methyl(7H-pyrrolo[2,3-d]pyrimidin-4-yl)amino]cyclohexyl}-N-1H-pyrazol-5-ylmethanesulfonamide;

N-(5-methyl-1H-pyrazol-3-yl)-1-{trans-4-[methyl(7H-pyrrolo[2,3-d]pyrimidin-4-yl)amino]cyclohexyl}methanesulfonamide;

N-1H-indol-5-yl-1-{trans-4-[methyl(7H-pyrrolo[2,3-d]pyrimidin-4-yl)amino]cyclohexyl}methanesulfonamide;

N-(6-chloropyridin-3-yl)-1-{trans-4-[methyl(7H-pyrrolo[2,3-d]pyrimidin-4-yl)amino]cyclohexyl}methanesulfonamide;

N-1H-indazol-5-yl-1-{trans-4-[methyl(7H-pyrrolo[2,3-d]pyrimidin-4-yl)amino]cyclohexyl}methanesulfonamide;

N-(3,4-dihydro-2H-1,5-benzodioxepin-7-yl)-1-{trans-4-[methyl(7H-pyrrolo[2,3-d]pyrimidin-4-yl)amino]cyclohexyl}methanesulfonamide;

N-(6-methoxypyridin-3-yl)-1-{trans-4-[methyl(7H-pyr-rolo[2,3-d]pyrimidin-4-yl)amino]cyclohexyl}methanesulfonamide;

N-(6-methylpyridin-3-yl)-1-{trans-4-[methyl(7H-pyrrolo[2,3-d]pyrimidin-4-yl)amino]cyclohexyl}methanesulfonamide;

N-[(2-methyl-1H-indol-5-yl)methyl]-1-{trans-4-[methyl(7H-pyrrolo[2,3-d]pyrimidin-4-yl)amino]cyclohexyl}methanesulfonamide;

N-[(5-methylpyrazin-2-yl)methyl]-1-{trans-4-[methyl(7H-pyrrolo[2,3-d]pyrimidin-4-yl)amino]cyclohexyl}methanesulfonamide;

1-{trans-4-[methyl(7H-pyrrolo[2,3-d]pyrimidin-4-yl)amino]cyclohexyl}-N-[(2R)-tetrahydrofuran-2-ylmethyl]methanesulfonamide;

N-[2-(6-methylpyridin-2-yl)ethyl]-1-{trans-4-[methyl(7H-pyrrolo[2,3-d]pyrimidin-4-yl)amino]cyclohexyl}methanesulfonamide;

N-[(4,6-dimethylpyrimidin-2-yl)methyl]-1-{trans-4-[methyl(7H-pyrrolo[2,3-d]pyrimidin-4-yl)amino]cyclohexyl}methanesulfonamide; and N-[(1,3-dimethyl-1H-pyrazol-4-yl)methyl]-1-{trans-4-[methyl(7H-pyrrolo[2,3-d]pyrimidin-4-yl)amino]cyclohexyl}methanesulfonamide; or a pharmaceutically acceptable salt thereof.

26. A pharmaceutical composition comprising a compound of Formula I or a pharmaceutically acceptable salt thereof.

* * * * *

UNITED STATES PATENT AND TRADEMARK OFFICE
CERTIFICATE OF CORRECTION

PATENT NO.         : 8,372,854 B2                                Page 1 of 1
APPLICATION NO.    : 12/964841
DATED              : February 12, 2013
INVENTOR(S)        : Jin Xie et al.

It is certified that error appears in the above-identified patent and that said Letters Patent is hereby corrected as shown below:

On the Title Page
Item (73), replace Madison, NJ with New York, NY

In the Claims
Column 60
Claim 2, line 11, replace (Cr  C6) with (C1-C6)
Claim 3, line 44, replace (Cr C6) with (C1-C6)

Column 65
Claim 25, line 25, replace rnethanesulfonamide with methanesulfonamide
Claim 25, line 28, replace rnethanesulfonamide with methanesulfonamide
Claim 25, line 37, replace rnethanesulfonamide with methanesulfonamide
Claim 25, line 40, replace rnethanesulfonamide with methanesulfonamide
Claim 25, line 43, replace rnethanesulfonamide with methanesulfonamide
Claim 25, line 46, replace rnethanesulfonamide with methanesulfonamide
Claim 25, line 49, replace rnethanesulfonamide with methanesulfonamide
Claim 25, line 52, replace rnethanesulfonamide with methanesulfonamide
Claim 25, line 55, replace rnethanesulfonamide with methanesulfonamide
Claim 25, line 58, replace rnethanesulfonamide with methanesulfonamide
Claim 25, line 61, replace rnethanesulfonamide with methanesulfonamide
Claim 25, line 67, replace rnethanesulfonamide with methanesulfonamide Signed and Sealed this
Seventh Day of October, 2014

Michelle K. Lee
*Deputy Director of the United States Patent and Trademark Office*

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial
<220> FEATURE:
<223> OTHER INFORMATION: FITC Synthetic Peptide

<400> SEQUENCE: 1

Lys Gly Gly Glu Glu Glu Glu Tyr Phe Glu Leu Val Lys Lys
1               5                   10

<210> SEQ ID NO 2
<211> LENGTH: 13
<212> TYPE: PRT
<213> ORGANISM: Artificial
<220> FEATURE:
<223> OTHER INFORMATION: 5-FAM Synthetic Peptide

<400> SEQUENCE: 2

Lys Lys Ser Arg Gly Asp Tyr Met Thr Met Gln Ile Gly
1               5                   10
```